US010092596B2

(12) United States Patent
Baumler et al.

(10) Patent No.: US 10,092,596 B2
(45) Date of Patent: Oct. 9, 2018

(54) TUNGSTATE TREATMENT OF THE DYSBIOSIS ASSOCIATED WITH GASTROINTESTINAL INFLAMMATION

(71) Applicant: THE REGENTS OF THE UNIVERSITY OF CALIFORNIA, Oakland, CA (US)

(72) Inventors: Andreas J. Baumler, Davis, CA (US); Sebastian E. Winter, Dallas, TX (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/964,487

(22) Filed: Dec. 9, 2015

(65) Prior Publication Data

US 2016/0158282 A1    Jun. 9, 2016

Related U.S. Application Data

(63) Continuation of application No. PCT/US2014/041571, filed on Jun. 9, 2014.

(60) Provisional application No. 61/833,396, filed on Jun. 10, 2013.

(51) Int. Cl.
*A61K 33/24* (2006.01)

(52) U.S. Cl.
CPC .................................... *A61K 33/24* (2013.01)

(58) Field of Classification Search
CPC ...................................................... A61K 33/24
USPC ......................................................... 424/617
See application file for complete search history.

(56) References Cited

U.S. PATENT DOCUMENTS

| 6,083,989 A | 7/2000 | Flitter et al. | |
|---|---|---|---|
| 2002/0052404 A1* | 5/2002 | Hunter | A61K 9/0024 514/449 |
| 2010/0247489 A1* | 9/2010 | Saur-Brosch | A61K 9/2846 424/93.4 |

FOREIGN PATENT DOCUMENTS

WO    2014/200929 A1    12/2014

OTHER PUBLICATIONS

The Written Opinion of the International Search Authority for the corresponding PCT/US2014/041571.*
Garrett el atl.; title: Enterobacteriaceae Act in Concert with the Gut Microbiota to Induce Spontaneous and Maternally Transmitted Colitis; Cell Host & Microbe, vol. 8, Issue 3, pp. 292-300, published Sep. 16, 2010.*
Friend, title: New oral delivery systems for treatment of inflammatory bowel disease; Adv Drug Deliv Rev., vol. 57, Issue 2, pp. 247-265, available online Sep. 27, 2004.*
Downs, Jane "The gastrointestinal tract and HIV pathogenesis," South African Journal of Clinical Nutrition, 2010, vol. 23, Iss. Supplement 1, pp. S65-S68.
Balagam et al., The mechanism of carbon dioxide catalysis in the hydrogen peroxide N-oxidation of amines, Inorganic chemistry, vol. 47, No. 3, Jan. 8, 2008, pp. 1173-1178.
Baraquet et al., Unexpected chemoreceptors mediate energy taxis towards electron acceptors in Shewanella oneidensis, Mol Microbiol, vol. 73, No. 2, 2009, pp. 278-290.
Barman et al., Enteric salmonellosis disrupts the microbial ecology of the murine gastrointestinal tract, Infect Immun, vol. 76, 2008, pp. 907-915.
Baumgart et al., Culture independent analysis of ileal mucosa reveals a selective increase in invasive *Escherichia coli* of novel phylogeny relative to depletion of Clostridiales in Crohn's disease involving the ileum, ISME J, vol. 1, 2007, pp. 403-418.
Berger et al., Lipocalin 2-deficient mice exhibit increased sensitivity to *Escherichia coli* infection but not to ischemia-reperfusion injury, Proc Natl Acad Sci U S A, vol. 103, No. 3, 2006, pp. 1834-1839.
Boirivant et al., Oxazolone colitis: A murine model of T helper cell type 2 colitis treatable with antibodies to interleukin 4, The Journal of experimental medicine, vol. 188, No. 10, 1998, pp. 1929-1939.
Bradley et al., Measurement of cutaneous inflammation: estimation of neutrophil content with an enzyme marker, J Invest Dermatol, vol. 78, 1982, pp. 206-209.
Carvalho et al., Crohn's disease-associated *Escherichia coli* LF82 aggravates colitis in injured mouse colon via signaling by flagellin. Inflammatory bowel diseases, Inflammatory bowel diseases, vol. 14, No. 8, 2008, pp. 1051-1060.
Clement et al., Microsomal N-oxygenation of adenine to adenine 1-N-oxide, Arch Pharm (Weinheim), vol. 326, No. 1, 1993, pp. 25-27.
Colome et al., Effect of N-acetylcysteine on the oxidative burst induced by phagocytosis of bacteria in human leukocytes, Methods and findings in experimental and clinical pharmacology, vol. 20, No. 4, 1998, pp. 301-305.
Darfeuille-Michaud et al., High prevalence of adherent-invasive *Escherichia coli* associated with ileal mucosa in Crohn's disease, Gastroenterology, vol. 127, No. 2, 2004, pp. 412-421.
Darfeuille-Michaud et al., Presence of adherent *Escherichia coli* strains in ileal mucosa of patients with Crohn's disease, Gastroenterology, vol. 115, No. 6, 1998, pp. 1405-1413.
De Groote et al., Genetic and redox determinants of nitric oxide cytotoxicity in a *Salmonella typhimurium* model, Proceedings of the National Academy of Sciences of the United States of America, vol. 92, 1995, pp. 6399-6403.

(Continued)

*Primary Examiner* — Yanzhi Zhang
(74) *Attorney, Agent, or Firm* — Kilpatrick Townsend & Stockton LLP

(57) ABSTRACT

The present invention provides compositions of therapeutic agents and methods of use for reducing and/or treating gastrointestinal inflammation. In particular aspects, the tungstate salts described herein and pharmaceutical compositions thereof inhibit the activity of one or a plurality of anaerobic respiratory enzymes in facultative anaerobic bacteria such as, for example, Enterobacteriaceae, that can exacerbate inflammation. In particular embodiments, the present invention provides compositions of therapeutic agents for treating gastrointestinal inflammation, as well as methods for treating or preventing gut microbial imbalance due to an increase in the abundance of intestinal Enterobacteriaceae.

9 Claims, 13 Drawing Sheets

(56) References Cited

OTHER PUBLICATIONS

De La Huerga et al., Urinary excretion of choline metabolites following choline administration in normals and patients with hepatobiliary diseases, The Journal of clinical investigation, vol. 30, 1951, pp. 463-470.

Dudhgaonkar et al., Influence of simultaneous inhibition of cyclooxygenase-2 and inducible nitric oxide synthase in experimental colitis in rats, Inflammopharmacology, vol. 15, 2007, pp. 188-195.

Eckburg et al., Diversity of the human intestinal microbial flora, Science, vol. 308, 2005, pp. 1635-1638.

Enocksson et al., Rectal nitric oxide gas and stool cytokine levels during the course of infectious gastroenteritis, Clinical and diagnostic laboratory immunology, vol. 11, No. 2, 2004, pp. 250-254.

Faith et al., Predicting a human gut microbiota's response to diet in gnotobiotic mice, Science, vol. 333, No. 6038, 2011, pp. 101-104.

Fischbach et al., Eating for two: how metabolism establishes interspecies interactions in the gut, Cell host & microbe, vol. 10, No. 4, 2011, pp. 336-347.

Flo et al., Lipocalin 2 mediates an innate immune response to bacterial infection by sequestrating iron, Nature, vol. 432, 2004, pp. 917-921.

Frank et al., Molecular-phylogenetic characterization of microbial community imbalances in human inflammatory bowel diseseases, Proc Natl Acad Sci U S A, vol. 104, No. 34, 2007, pp. 3780-13785.

Garrett et al., Communicable ulcerative colitis induced by T-bet deficiency in the innate immune system, Cell, vol. 131, No. 1, 2007, pp. 33-45.

Garrett et al., Enterobacteriaceae Act in Concert with the Gut Microbiota to Induce Spontaneous and Maternally Transmitted Colitis, Cell Host & Microbe, Sep. 16, 2010, vol. 8, pp. 292-300.

Gennis et al., Respiration, in Neidhardt for *Escherichia coli* and *Salmonella*,Cellular and molecular biology, Section A2, Energy Production, 1996, 2nd ed, vol. 1. ASM Press, Washington, D.C., pp. 217-261.

Giaffer et al., The assessment of faecal flora in patients with inflammatory bowel disease by a simplified bacteriological technique, Journal of medical microbiology, vol. 35, No. 4, 1991, pp. 238-243.

Goetz et al., The neutrophil lipocalin NGAL is a bacteriostatic agent that interferes with siderophore-mediated iron acquisition, Mol Cell, vol. 10, No. 5, 2002, pp. 1033-1043.

Gophna et al., Differences between tissue-associated intestinal microfloras of patients with Crohn's disease and ulcerative colitis, J Clin Microbiol, vol. 44, No. 11, 2006, pp. 4136-4141.

Guandalini et al., Tissue distribution of tungsten in mice following oral exposure to sodium tungstate, Chemical research in toxicology, vol. 24, No. 4, 2011, pp. 488-493.

Gutthann et al., Inhibition of respiration and nitrate assimilation enhances photohydrogen evolution under low oxygen concentrations in *Synechocystis* sp. PCC 6803, Biochim Biophys Acta., vol. 1767, No. 2, 2007, pp. 161-169.

Hanzu et al., Proof-of-concept trial on the efficacy of sodium tungstate in human obesity, Diabetes, obesity & metabolism, vol. 12, No. 11, 2010, pp. 1013-1018.

Harper et al., Differential regulation of dual NADPH oxidases/peroxidases, Duox1 and Duox2, by Th1 and Th2 cytokines in respiratory tract epithelium, FEBS letters, vol. 579, No. 21, 2005, pp. 4911-4917.

Hartman, Human gut microbiome adopts an alternative state following small bowel transplantation, Proc Natl Acad Sci U S A, vol. 106, No. 40, 2009, pp. 17187-17192.

Hohn et al., NADPH oxidase deficiency in X-linked chronic granulomatous disease, The Journal of clinical investigation, vol. 55, No. 4, 1975, pp. 707-713.

Jagannath et al., Induction of nitric oxide in human monocytes and monocyte cell lines by *Mycobacterium tuberculosis*, Nitric oxide: biology and chemistry / official journal of the Nitric Oxide Society, vol. 2, No. 3, 1998, pp. 174-186.

Jones et al., Anaerobic respiration of *Escherichia coli* in the mouse intestine, Infection and immunity, vol. 79, No. 10, 2011, pp. 4218-4242.

Kitajima et al., Dextran sodium sulfate-induced colitis in germ-free IQI/Jic mice, Exp Anim, vol. 50, No. 5, 2001, pp. 387-395.

Koch et al., Effects of N-acetylcysteine on bacterial clearance, European journal of clinical investigation, vol. 26, No. 10, 1996, pp. 884-892.

Koropatkin et al., How glycan metabolism shapes the human gut microbiota, Nature reviews, Microbiology, vol. 10, No. 5, 2012, pp. 323-335.

Krook et al., Relation between concentrations of metronidazole and *Bacteroides* spp in faeces of patients with Crohn's disease and healthy individuals, Journal of clinical pathology, vol. 34, No. 6, 1981, pp. 645-650.

Kuwano et al., Interferon-gamma activates transcription of NADPH oxidase 1 gene and upregulates production of superoxide anion by human large intestinal epithelial cells, American journal of physiology, Cell physiology, vol. 290, No. 2, 2006, pp. C433-C443.

Ley et al., Obesity alters gut microbial ecology, Proceedings of the National Academy of Sciences of the United States of America, vol. 102, No. 31, 2005, pp. 11070-11075.

Lundberg et al., Greatly increased luminal nitric oxide in ulcerative colitis, Lancet, vol. 344, No. 8938, 1994, pp. 1673-1674.

Lupp et al., Host-mediated inflammation disrupts the intestinal microbiota and promotes the overgrowth of Enterobacteriaceae, Cell Host Microbe, vol. 2, No. 2, 2007, pp. 119-129.

Mahowald et al., Characterizing a model human gut microbiota composed of members of its two dominant bacterial phyla, Proceedings of the National Academy of Sciences of the United States of America, vol. 106, No. 14, 2009, pp. 5859-5864.

Martinez et al., Resistant starches types 2 and 4 have differential effects on the composition of the fecal microbiota in human subjects, PloS one, vol. 5, No. 11, 2010, p. e15046.

Masoodi et al., Fecal lactoferrin, myeloperoxidase and serum C-reactive are effective biomarkers in the assessment of disease activity and severity in patients with idiopathic ulcerative colitis, J Gastroenterol Hepatol, vol. 24, No. 11, 2009, pp. 1768-1774.

McPhail et al., Deficiency of NADPH oxidase activity in chronic granulomatous disease, The Journal of pediatrics, vol. 90, No. 2, 1977, pp. 213-217.

Nagy et al., Effect of the mucoactive drug nacystelyn on the respiratory burst of human blood polymorphonuclear neutrophils, Pulmonary pharmacology & therapeutics, vol. 10, No. 5-6, 1997, pp. 287-292.

Palmer et al., Vascular endothelial cells synthesize nitric oxide from L-arginine, Nature, vol. 333, No. 6174, 1988, pp. 664-666.

Peterson et al., Metagenomic approaches for defining the pathogenesis of inflammatory bowel diseases, Cell host & microbe, vol. 3, No. 6, 2008, pp. 417-427.

Raffatellu et al., Lipocalin-2 resistance confers an advantage to *Salmonella enterica* serotype Typhimurium for growth and survival in the inflamed intestine, Cell Host Microbe, vol. 5, No. 5, 2009, pp. 476-486.

Sadlack et al., Ulcerative colitis-like disease in mice with a disrupted interleukin-2 gene, Cell, vol. 75, No. 2, 1993, pp. 253-261.

Sadowska et al., Effect of N-acetylcysteine on neutrophil activation markers in healthy volunteers: in vivo and in vitro study, Pharmacological research : the official journal of the Italian Pharmacological Society, vol. 53, No. 3, 2006, pp. 216-225.

Salzman et al., Induction and activity of nitric oxide synthase in cultured human intestinal epithelial monolayers, The American journal of physiology, vol. 270, 1996, pp. G565-G573.

Schoneich et al., Methionine oxidation by reactive oxygen species: reaction mechanisms and relevance to Alzheimer's disease, Biochimica et biophysica acta, vol. 1703, No. 2, 2005, pp. 111-119.

Seger et al., Chronic granulomatous disease due to granulocytes with abnormal NADPH oxidase activity and deficient cytochrome-b, Blood, vol. 61, No. 3, 1983, pp. 423-428.

Seksik et al., Alterations of the dominant faecal bacterial groups in patients with Crohn's disease of the colon, Gut, vol. 52, No. 2, 2003, pp. 237-242.

(56) References Cited

OTHER PUBLICATIONS

Sellon et al., Resident enteric bacteria are necessary for development of spontaneous colitis and immune system activation in interleukin-10-deficient mice, Infect Immun, vol. 66, No. 11, 1998, pp. 5224-5231.

Singer et al., Expression of inducible nitric oxide synthase and nitrotyrosine in colonic epithelium in inflammatory bowel disease, Gastroenterology, No. 111, No. 4, 1996, pp. 871-785.

Sonnenburg et al., Specificity of polysaccharide use in intestinal *bacteroides* species determines diet-induced microbiota alterations, Cell, vol. 141, No. 7, 2010, pp. 1241-1252.

Stecher et al., Like will to like: abundances of closely related species can predict susceptibility to intestinal colonization by pathogenic and commensal bacteria, PLoS pathogens, vol. 6, No. 1, 2010, pp. 1-15.

Stecher et al., *Salmonella enterica serovar typhimurium* exploits inflammation to compete with the intestinal microbiota, PLoS Biol, vol. 5, No. 10, 2007, pp. 2177-2189.

Stewart et al., Identification and expression of genes narL and narX of the nar (nitrate reductase) locus in *Escherichia coli* K-12, J Bacteriol, vol. 170, No. 4, 1988, pp. 1589-1597.

Stewart et al., Periplasmic nitrate reductase (NapABC enzyme) supports anaerobic respiration by *Escherichia coli* K-12, J Bacteriol, vol. 184, No. 5, 2002, pp. 1314-1323.

Szabo et al., Peroxynitrite: biochemistry, pathophysiology and development of therapeutics, Nat Rev Drug Discov, Nature Reviews, Aug. 2007, vol. 6, pp. 662-680.

Takahashi et al., Tungstate as competitive inhibitor of molybdate in nitrate assimilation and in N2 fixation by Azotobacter, Biochimica et biophysica acta, vol. 23, No. 2, 1957, pp. 433-435.

Thiennimitr et al., Intestinal inflammation allows *Salmonella* to use ethanolamine to compete with the microbiota, Proceedings of the National Academy of Sciences of the United States of America, vol. 108, No. 42, 2011, pp. 17480-17485.

Walker et al., Dominant and diet-responsive groups of bacteria within the human colonic microbiota, The ISME journal, vol. 5, No. 2, 2011, pp. 220-230.

Winter et al., Gut inflammation provides a respiratory electron acceptor for *Salmonella*, Nature, No. 467, 2010, pp. 426-429.

Winter et al., Host-derived nitrate boosts growth of *E. coli* in the inflamed gut, Science:in press, vol. 339, No. 6120, 2013, pp. 708-711.

Wu et al., Linking long-term dietary patterns with gut microbial enterotypes, Science, vol. 334, No. 6052, 2011, pp. 105-108.

Zhu et al., Bactericidal activity of peroxynitrite, Archives of biochemistry and biophysics, vol. 298, No. 2, 1992, pp. 452-457.

Zhu et al., "Precision editing of the gut microbiota ameliorates colitis," Nature, Letter, Jan. 11, 2018, vol. 553, pp. 208-211, doi 10.1038/nature25172.

* cited by examiner

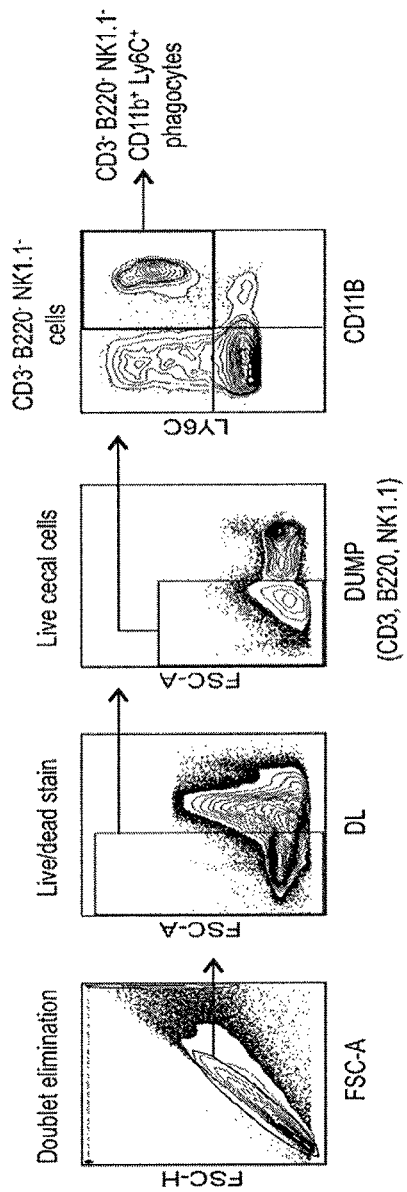
FIG. 7A
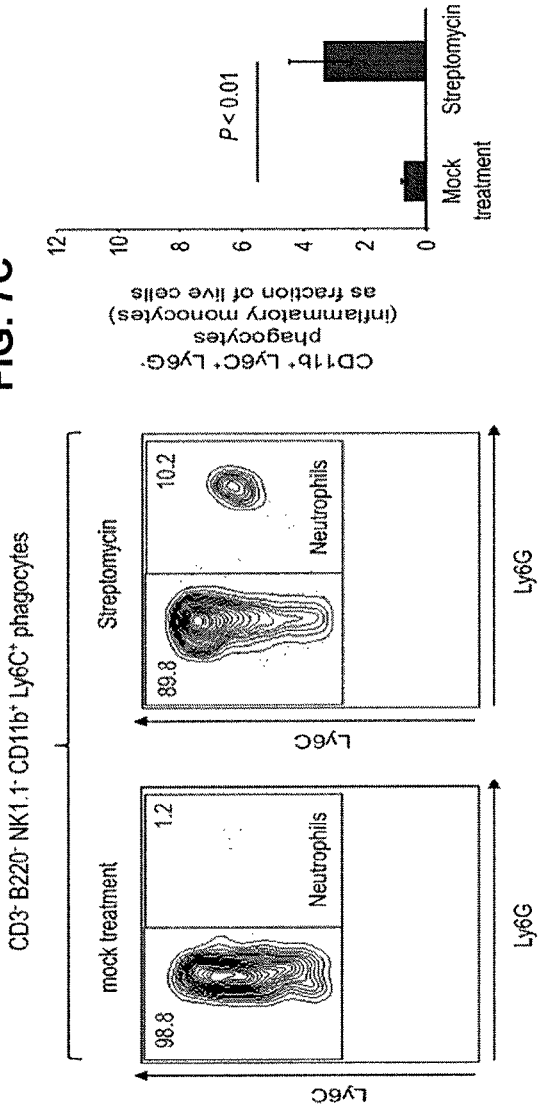
FIG. 7B
FIG. 7C

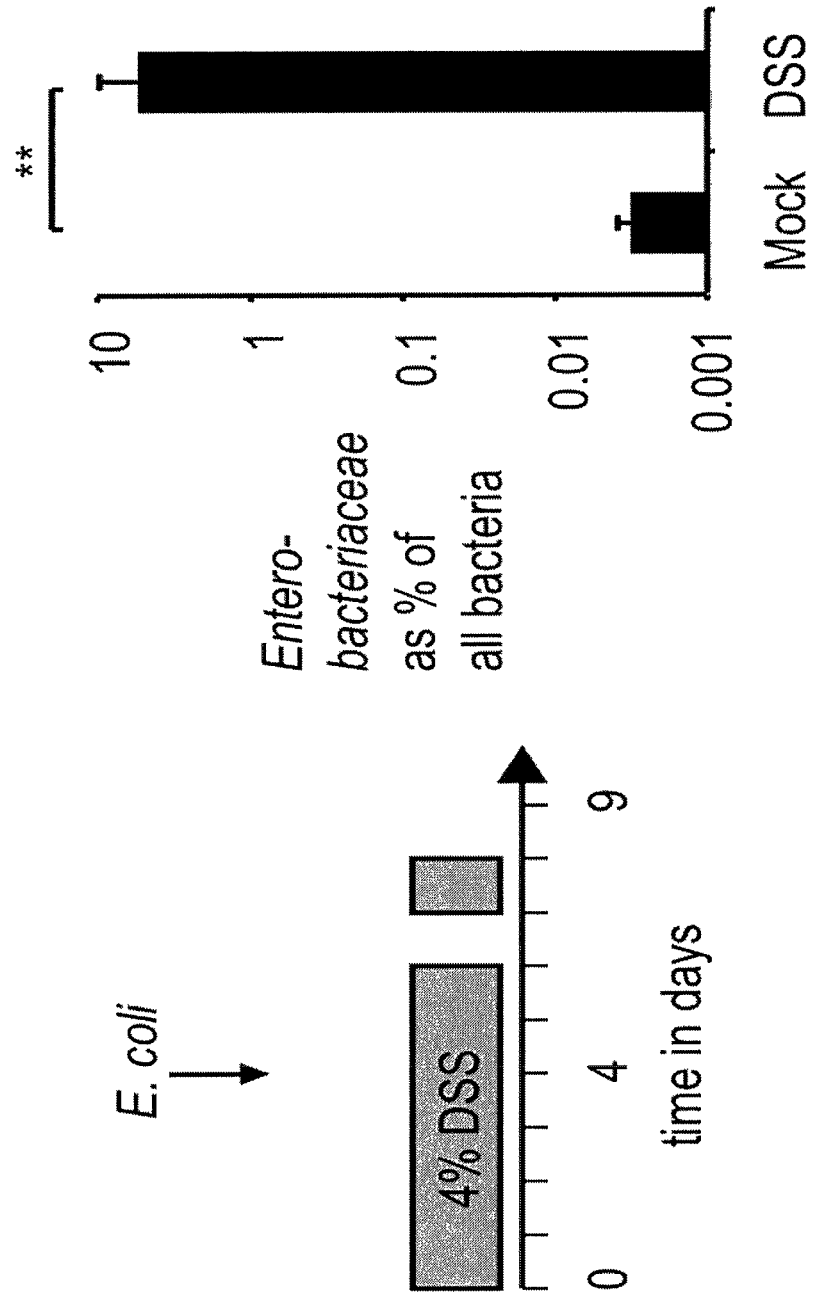

TUNGSTATE TREATMENT OF THE DYSBIOSIS ASSOCIATED WITH GASTROINTESTINAL INFLAMMATION

CROSS-REFERENCES TO RELATED APPLICATIONS

This application is a continuation of PCT/US2014/041571, filed Jun. 9, 2014, which application claims priority to U.S. Provisional Application No. 61/833,396, filed Jun. 10, 2013, the disclosures of which are hereby incorporated by reference in their entirety for all purposes.

STATEMENT AS TO RIGHTS TO INVENTIONS MADE UNDER FEDERALLY SPONSORED RESEARCH AND DEVELOPMENT

This invention was made with Government support under Grant No. AI096528, awarded by the National Institutes of Health. The Government has certain rights in the invention.

BACKGROUND OF THE INVENTION

Over 90% of the cells in the human body are microbes, the majority of which reside in bacterial communities (microbiota) that inhabit the large intestine. Recent advances in high-throughput microbiota sequencing (metagenomics) provide a powerful tool for profiling the previously hidden microbial diversity in the gut. For example, metagenomic analysis shows that the large intestine is host to a diverse bacterial community whose structure, at the phylum level, is maintained through unknown mechanisms. The bacterial species dominating the microbiota in the large bowel are strict anaerobes, which lack the ability to respire oxygen and rely on fermentation of complex polysaccharides for growth (Mahowald et al., Proc. Natl. Acad. Sci. U.S.A., 106:5859-5864 (2009)). Towering above all other are obligate anaerobic bacteria belonging to the phyla Bacteroidetes (class Bacteroidia) and Firmicutes (class Clostridia) (Eckburg et al., Science, 308:1635-1638 (2005)). The dominance of obligate anaerobic bacteria belonging to the classes Bacteroidia and Clostridia is a conserved feature of bacterial communities inhabiting the large intestine of both humans and mice (Eckburg et al., Science, 308:1635-1638 (2005); Ley et al., Proc. Natl. Acad. Sci. U.S.A., 102:11070-11075 (2005)).

However, conditions of gastrointestinal inflammation can lead to a microbial imbalance (dysbiosis) characterized by phylum-level changes in the microbiota composition, including a marked decrease in the representation of obligate anaerobic bacteria and an increased relative abundance of facultative anaerobic bacteria. For example, acute intestinal inflammation triggered by pathogenic Enterobacteriaceae (class Gammaproteobacteria, phylum Proteobacteria), such as Salmonella enterica or Citrobacter rodentium, is accompanied by changes in the bacterial community structure that are marked by an outgrowth of the respective facultative anaerobic pathogen (Barman et al., Infect. Immun., 76:907-915 (2008); Lupp et al, Cell Host Microbe, 2:119-129 (2007); Stecher et al., PLoS Biol., 5:2177-2189 (2007)). Similarly, a reduced relative abundance of strictly anaerobic members of the classes Bacteroidia and Clostridia, and a concomitant increased relative abundance of facultative anaerobic commensal bacteria belonging to the family Enterobacteriaceae or to the class Bacilli (phylum Firmicutes) is seen in individuals with inflammatory bowel disease (IBD) (Baumgart et al., ISME J., 1:403-418 (2007); Frank et al., Proc. Natl. Acad. Sci U.S.A., 104:13780-13785 (2007); Giaffer et al., J. Med. Microbiol., 35:238-243 (1991); Gophna et al., J. Clin. Microbiol., 44:4136-4141 (2006); Krook et al., J. Clinical Pathology, 34:645-650 (1981); Seksik et al., Gut, 52:237-242 (2003); Walker et al., ISME J., 5:220-230 (2011)).

A marked decrease in the representation of obligate anaerobic Bacteroidia and Clostridia and an increased relative abundance of facultative anaerobic Enterobacteriaceae can also be observed in mice when colitis is induced chemically (Lupp et al., Cell Host Microbe, 2:119-129 (2007)) or through genetically engineered immune defects (Garrett et al., Cell Host Microbe, 8:292-300 (2010)). The dense bacterial communities inhabiting the distal gut compete fiercely for a limited quantity of diet-derived or host mucus-derived carbohydrate available for fermentation (reviewed in, e.g., Fischbach and Sonnenburg, Cell Host Microbe, 10:336-347 (2011); Koropatkin et al., Nat. Rev. Microbiology, 10:323-335 (2012)). Changes in the diet can alter the microbial community structure on the species level; however, the dominance of obligate anaerobic Clostridia and Bacteroidia over the facultative anaerobic Enterobacteriaceae remains untouched (Faith et al., Science, 333:101-104 (2011); Martinez et al., PLoS One, 5:e15046; Sonnenburg et al., Cell, 141:1241-1252 (2010); Walker et al., ISME J., 5:220-230 (2011); Wu et al., Science, 334:105-108 (2011)).

Thus, a need exists for therapeutic agents and methods for inhibiting anaerobic respiration by gut microbes, thereby reducing gastrointestinal inflammation. The present invention satisfies this need and provides related advantages as well.

BRIEF SUMMARY OF THE INVENTION

In one aspect, the present invention provides a method for treating dysbiosis in a subject having gastrointestinal inflammation. In some embodiments, the method comprises administering to the subject a therapeutically effective amount of a tungstate salt.

In particular embodiments, the gastrointestinal inflammation comprises inflammatory bowel disease (IBD). Non-limiting examples of IBD include ulcerative colitis (UC), Crohn's disease (CD), indeterminate colitis (IC), and combinations thereof. In other embodiments, the gastrointestinal inflammation comprises colitis. In further embodiments, the gastrointestinal inflammation comprises an HIV enteropathy.

In some embodiments, an increased amount of Enterobacteriaceae is present in the subject's gastrointestinal tract.

In certain embodiments, the tungstate salt is selected from sodium tungstate, potassium tungstate, magnesium tungstate, calcium tungstate, and mixtures thereof. In some embodiments, the tungstate salt is formulated as a pharmaceutical composition.

In some embodiments, the therapeutically effective amount of the tungstate salt is substantially equivalent to (e.g., provides the same or similar therapeutic effect as) a dosing regimen of about 100 mg twice daily for about 6 weeks. In other embodiments, the tungstate salt is administered orally.

In another aspect, the present invention provides a method for preventing dysbiosis in a subject having or suspected of having gastrointestinal inflammation. In some embodiments, the method comprises administering to the subject a therapeutically effective amount of a tungstate salt. In some embodiments, the subject does not have symptoms of inflammation-associated dysbiosis.

In particular embodiments, the gastrointestinal inflammation comprises inflammatory bowel disease (IBD). Non-limiting examples of IBD include ulcerative colitis (UC), Crohn's disease (CD), indeterminate colitis (IC), and combinations thereof. In other embodiments, the gastrointestinal inflammation comprises colitis. In further embodiments, the gastrointestinal inflammation comprises an HIV enteropathy.

In certain embodiments, the tungstate salt is selected from sodium tungstate, potassium tungstate, magnesium tungstate, calcium tungstate, and mixtures thereof. In some embodiments, the tungstate salt is formulated as a pharmaceutical composition.

In some embodiments, the therapeutically effective amount of the tungstate salt is substantially equivalent to about 100 mg twice daily for about 6 weeks. In other embodiments, the tungstate salt is administered orally.

In yet another aspect, the present invention provides a method for reducing the abundance of Enterobacteriaceae in a subject with gastrointestinal inflammation. The method comprises administering to the subject a therapeutically effective amount of a tungstate salt.

In certain embodiments, the abundance of Enterobacteriaceae present in the subject's gastrointestinal tract is reduced by at least about 50% compared to a control. In certain other embodiments, the abundance of Enterobacteriaceae present in the subject's gastrointestinal tract is reduced by at least about 80% compared to a control. In some embodiments, the control is the abundance of Enterobacteriaceae in the subject's gastrointestinal tract prior to receiving the tungstate salt.

In particular embodiments, the gastrointestinal inflammation comprises inflammatory bowel disease (IBD). Non-limiting examples of IBD include ulcerative colitis (UC), Crohn's disease (CD), indeterminate colitis (IC), and combinations thereof. In other embodiments, the gastrointestinal inflammation comprises colitis. In further embodiments, the gastrointestinal inflammation comprises an HIV enteropathy.

In certain embodiments, the tungstate salt is selected from sodium tungstate, potassium tungstate, magnesium tungstate, calcium tungstate, and mixtures thereof. In some embodiments, the tungstate salt is formulated as a pharmaceutical composition.

In some embodiments, the therapeutically effective amount of the tungstate salt is substantially equivalent to about 100 mg twice daily for about 6 weeks. In other embodiments, the tungstate salt is administered orally.

In another aspect, the present invention provides a method for restoring a normal microbial community structure in the gastrointestinal tract of a subject having gastrointestinal inflammation. The method comprises administering to the subject a therapeutically effective amount of a tungstate salt.

In some embodiments, the therapeutically effective amount of a tungstate salt decreases the abundance of Enterobacteriaceae in the subject's gastrointestinal tract to the abundance thereof in a subject not having or suspected of having the gastrointestinal inflammation.

In particular embodiments, the gastrointestinal inflammation comprises inflammatory bowel disease (IBD). Non-limiting examples of IBD include ulcerative colitis (UC), Crohn's disease (CD), indeterminate colitis (IC), and combinations thereof. In other embodiments, the gastrointestinal inflammation comprises colitis. In further embodiments, the gastrointestinal inflammation comprises an HIV enteropathy.

In certain embodiments, the tungstate salt is selected from sodium tungstate, potassium tungstate, magnesium tungstate, calcium tungstate, and mixtures thereof. In some embodiments, the tungstate salt is formulated as a pharmaceutical composition.

In some embodiments, the therapeutically effective amount of the tungstate salt is substantially equivalent to about 100 mg twice daily for about 6 weeks. In other embodiments, the tungstate salt is administered orally.

In yet another aspect, the present invention provides a method for reducing gastrointestinal inflammation in a subject in need thereof. The method comprises administering to the subject a therapeutically effective amount of a tungstate salt.

In particular embodiments, the gastrointestinal inflammation comprises inflammatory bowel disease (IBD). Non-limiting examples of IBD include ulcerative colitis (UC), Crohn's disease (CD), indeterminate colitis (IC), and combinations thereof. In other embodiments, the gastrointestinal inflammation comprises colitis. In further embodiments, the gastrointestinal inflammation comprises an HIV enteropathy.

In some embodiments, the therapeutically effective amount of the tungstate salt reduces the gastrointestinal inflammation by reducing the abundance of Enterobacteriaceae in the subject's gastrointestinal tract. In certain embodiments, the abundance of Enterobacteriaceae in the subject's gastrointestinal tract is reduced by at least about 50% compared to a control. In certain other embodiments, the abundance of Enterobacteriaceae in the subject's gastrointestinal tract is reduced by at least about 80% compared to a control. In some embodiments, the control is the abundance of Enterobacteriaceae in the subject's gastrointestinal tract prior to receiving the tungstate salt.

In certain embodiments, the tungstate salt is selected from sodium tungstate, potassium tungstate, magnesium tungstate, calcium tungstate, and mixtures thereof. In some embodiments, the tungstate salt is formulated as a pharmaceutical composition.

In some embodiments, the therapeutically effective amount of the tungstate salt is substantially equivalent to about 100 mg twice daily for about 6 weeks. In other embodiments, the tungstate salt is administered orally.

Other objects, features, and advantages of the present invention will be apparent to one of skill in the art from the following detailed description and figures.

BRIEF DESCRIPTION OF THE DRAWINGS

FIG. 3A shows detection of nitrate reductase activity in E. coli strains. FIG. 3B shows competitive indices for anaerobic growth in mucin broth with (+) or without (−) nitrate (n=3). Bars represent geometric means±standard error. **, $P<0.01$.

FIGS. 7A-C show an analysis of cellular infiltrates in the cecal mucosa after streptomycin treatment using flow cytometry. Mice were treated with streptomycin (n=4) or mock-treated (n=4) and a single cell suspension was generated from the cecum 96 hours later. FIG. 7A depicts the gating strategy. Forward scatter height (FSC-H) and forward scatter area (FSC-A) were used for doublet elimination of $4 \times 10^6$ cecal cells (left panel). Dead cells were excluded based on Dead/Live Aqua staining (DL; Life Technologies, Carlsbad, Calif.) (second panel from the left). Live cecal cells were gated on the "dump channel" negative population. Markers in the dump channel included CD3 (T cell marker), B220 (B cell marker) and NK1.1 (NK and NKT cell marker) (second panel from the right). The "dump channel" negative population was gated into CD11B positive and Ly6C positive phagocytes (right panel). All gates were based on Fluorescence-Minus-One controls. FIG. 7B shows the detection of neutrophils ($Ly6G^+$ cells) among $CD3^-B220^-NK1.1^-CD11b^+Ly6C^+$ phagocytes. Gating was based on Fluorescence-Minus-One controls. FIG. 7C shows that inflammatory monocytes ($CD3^-B220^-NK1.1^-CD11b^+Ly6C^+Ly6G^-$ cells) are a fraction of live cecal cells.

FIGS. 8A-B show samples from mock-treated mice (Mock) or DSS-treated mice (DSS) five days after inoculation with E. coli. FIG. 8A shows a schematic of DSS treatment and E. coli inoculation regiments used. FIG. 8B shows that E. coli is a small percentage of the total cecal bacterial population, as determined by 16S rRNA gene qRT-PCR. **, $P<0.01$.

DETAILED DESCRIPTION OF THE INVENTION

I. Introduction

The lumen of the distal gut is a fairly anaerobic environment. Traces of oxygen present in this habitat are readily consumed by facultative anaerobic bacteria (e.g., Enterobacteriaceae), which constitute a small fraction (approximately 0.1%) of the microbiota (Eckburg et al., *Science*, 308:1635-1638 (2005)). The amount of available oxygen seems to limit the growth of Enterobactericeae in this environment, because elevated oxygen levels increase their relative abundance. For example, the ileostomy of small bowel transplant patients provides a portal that allows oxygen to reach the otherwise anaerobic distal ileum. An increase in the relative abundance of Enterobacteriaceae is observed in close proximity to the ileostomy and the microbial community returns to its normal composition after surgical closure of the ileostomy (Hartman et al., *Proc. Natl. Acad. Sci. U.S.A.*, 106:17187-17192 (2009)). Thus, once the available oxygen is consumed, Enterobacteriaceae are apparently poorly equipped to compete with obligate anaerobic bacteria for high-energy nutrients to support their growth by fermentation.

Intestinal inflammation is accompanied by the release of antimicrobials, a host defense mechanism designed to eradicate microbes from tissue or from close vicinity to the epithelium. Some antimicrobials function in nutrient withholding by interfering with microbial acquisition of trace elements, such as iron or zinc. For example, upon stimulation with IL-22 epithelial cells release the antimicrobial lipocalin-2 into the intestinal lumen (Raffatellu et al., *Cell Host Microbe*, 5:476-486 (2009)). Lipocalin-2 binds enterobactin, thereby preventing bacteria from using this siderophore for iron acquisition (Berger et al., *Proc. Natl. Acad. Sci. U.S.A.*, 103:1834-1839 (2006), Flo et al., *Nature*, 432: 917-921 (2004), Goetz et al., *Mol. Cell.*, 10:1033-1043 (2002)). The release of lipocalin-2 can provide a selective advantage for enteric pathogens that possess specific lipocalin-2 resistance mechanisms (Raffatellu et al., *Cell Host Microbe*, 5:476-486 (2009)). However, many commensal Enterobacteriaceae are susceptible to lipocalin-2, suggesting that release of this antimicrobial is not likely responsible for the phylum-level changes in microbial communities associated with gut inflammation.

Figure 1:
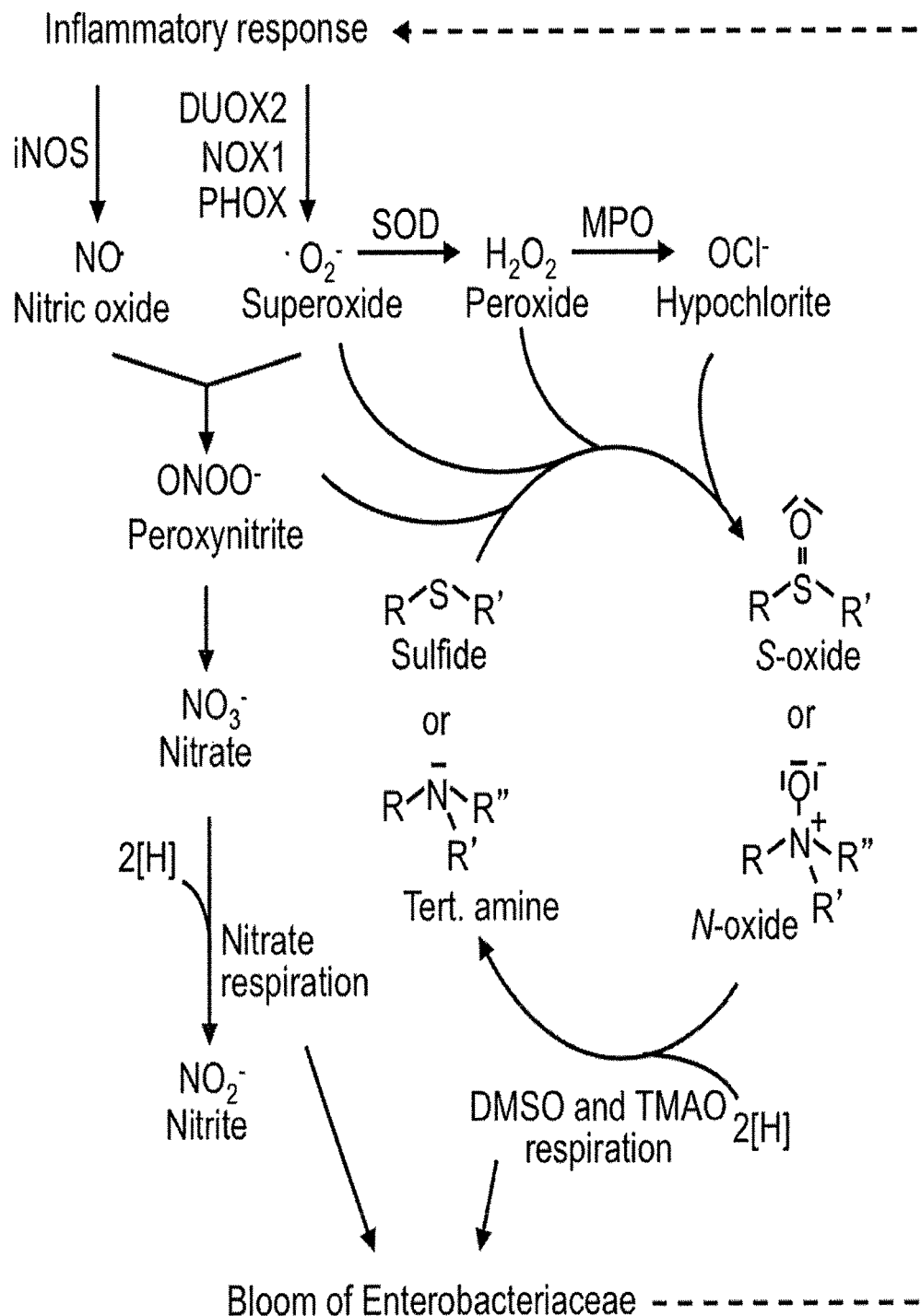
FIG. 1 illustrates a schematic diagram of inflammation dependent anaerobic respiration of Enterobacteriaceae.

A second group of antimicrobials produced during inflammation are reactive oxygen species (ROS) and reactive nitrogen species (RNS). Upon stimulation with pro-inflammatory cytokines, such as interferon (IFN)-γ, the intestinal epithelium can produce superoxide radicals ($O_2^-$) by activating dual function NAD(P)H oxidase 2 (DUOX2) (Harper et al., *FEBS Letters*, 579:4911-4917 (2005)). See, FIG. 1. In addition, IFN-γ induces expression of the NADPH oxidase 1 (Nox1) gene, encoding a second NADPH oxidase of epithelial cells (Kuwano et al., *Am. J. Physiol. Cell Physiol.*, 290:C433-C443 (2006)). Severe intestinal inflammation can be accompanied by transmigration of neutrophils into the intestinal lumen and subsequent generation of superoxide radicals by the phagocyte NADPH oxidase (PHOX). The generation of superoxide radicals by phagocytes is essential for host defense, as illustrated by recurrent bacterial infections in individuals with chronic granulomatous disease, an illness brought about by PHOX-deficiency (Hohn et al., *J. Clin. Invest.*, 55:707-713 (1975); McPhail et al., *J. Pediatr.*, 90:213-317 (2997); Seger et al., *Blood*, 61:423-428 (1983)). Neutrophils also express superoxide dismutase (SOD) and myeloperoxidase (MPO), which convert superoxide radicals to hydrogen peroxide ($H_2O_2$) and hypochlorite ($OCl^-$). Furthermore, stimulation with IFN-γ can induce expression of the Nos2 gene in the intestinal epithelium (Salzman et al., *Am. J. Physiol.*, 270:G565-G573). The enzyme encoded by Nos2, inducible nitric oxide synthase (iNOS), catalyzes the production of nitric oxide (NO.) from L-arginine (Palmer et al., *Nature*, 333:664-666 (1998)). Phagocytes recruited to the gut mucosa during inflammation are another cellular source of iNOS (Jagannath et al., *Nitric Oxide*, 2:174-186 (1998)). Elevated levels of iNOS during inflammation can alter the luminal environment of the large bowel, as indicated by raised nitric oxide concentrations in colonic luminal gas of individuals with inflammatory bowel disease (Enocksson et al., *Clin. Diagn. Lab Immunol.*, 11:250-254 (2004); Lundberg et al., *Lancet*, 344:1673-1374 (1994); Singer et al., *Gastroenterology*, 111:871-885 (1996)). Finally, reaction of nitric oxide with a superoxide radical gives rise to peroxynitrite ($ONOO^-$), a potent bactericidal RNS (De Groote et al., *Proc. Natl. Acad. Sci. U.S.A.*, 92:6399-6403 (1995); Zhu et al., *Arch. Biochem. Biophys.*, 298:452-457 (1992)).

While the production of RNS and ROS creates a hostile environment in close proximity to the mucosal surface, generation of these radicals has important side effects. As peroxynitrite, superoxide, hydrogen peroxide and hypochlorite diffuse away from the epithelium, these radicals quickly react with organic sulfides and tertiary amines present in the intestinal lumen to form the respective S-oxides and N-oxides (Balagam et al., *Inorg. Chem.*, 47:1173-1178 (2008); Schoneich et al., *Biochim. Biophys. Acta.*, 1703:111-119 (2005)). See, FIG. 1. For example, when dietary contents have been flushed out by diarrhea, enterocytes released from the tips of villi are the main source of membrane lipids, such as phosphatidylcholine and sphingomyelin, in the intestinal lumen. A nutrient derived from phosphatidylcholine or sphingomyelin is choline. Choline is degraded by the gut microbiota to trimethylamine (TMA) (de la Huerga et al., *J. Clin. Invest.*, 30:463-470 (1951)), a compound that can be oxidized by peroxynitrite, superoxide, hydrogen peroxide or hypochlorite to trimethylamine N-oxide (TMAO) (Balagam et al., *Inorg. Chem.*, 47:1173-1178 (2008); Schoneich et al., *Biochim. Biophys. Acta.*, 1703:111-119 (2005)). Alternatively, peroxynitrite can be converted to nitrate ($NO_3^-$) in a reaction catalyzed by carbon dioxide ($CO_2$) (Szabo et al., *Nat. Rev. Drug Discov.*, 6:662-680 (2007)). As a result, nitrate production in the gut lumen is a by-product of chemically-induced colitis (Dudhgaonkar et al., *Inflammopharmocology*, 15:188-195 (2007)). Ultimately, these processes convert bactericidal RNS and ROS into non-toxic products (i.e., S-oxides, N-oxides and nitrate) whose presence causes a dramatic change in the growth conditions encountered in the distal gut.

The lumen of the large bowel is largely devoid of exogenous electron acceptors that would support growth by anaerobic respiration. As a result, fermentation of carbohydrates is the main strategy by which microbial communities in the healthy large intestine support their anaerobic growth. However, the generation of S-oxides, N-oxides and nitrate as by-products of the host inflammatory response opens a new alternative for facultative anaerobic microbes to grow in this environment. Enterobacteriaceae can use S-oxides, N-oxides and nitrate as terminal electron acceptors for anaerobic respiration by expressing dimethyl S-oxide (DMSO) reductases, TMAO reductases and nitrate reductases, respectively (see, e.g., Gennis, R. B., and V. Stewart., "Respiration", p. 217-261. In *Escherichia coli* and *Salmonella*. Cellular and Molecular Biology, 2nd ed, vol. 1. ASM Press, Washington, D.C. (1996)). In contrast, Clostridia and Bacteroidia possess only a primitive electron transport chain and lack the terminal oxidoreductases needed to utilize exogenous electron acceptors generated during inflammation (Fischbach et al., *Cell Host Microbe*, 10:336-347 (2011)).

Gastrointestinal inflammation enables Enterobacteriaceae to support its growth by anaerobic respiration, which is more efficient for energy production than fermentation. Furthermore, anaerobic respiration makes it possible to utilize carbon sources that do not support growth by fermentation. Intestinal inflammation has been shown to enable Enterobacteriaceae to sidestep nutritional competition with the obligate anaerobic Clostridia and Bacteroidia in the large bowel (Winter et al., *Science*, 339:708-711 (2013)). In turn, the fitness advantage gained by Enterobacteriaceae through anaerobic respiration gives rise to the phylum-level changes in the microbiota composition observed during gut inflammation.

Current treatment options for diseases associated with gastrointestinal inflammation such as inflammatory bowel disease (IBD) include anti-inflammatory therapy, such an anti-TNF-alpha antibodies. However, these therapies have significant side-effects. The present invention is advantageous because it provides methods for treating gastrointestinal inflammation such as IBD that are much better tolerated than conventional approaches. In particular embodiments, the present invention provides therapeutic agents for treating gastrointestinal inflammation, as well as methods for treating or preventing gut microbial imbalance due to, for example, an increase in gut Enterobacteriaceae. The present inventors have discovered that tungstate, an oxide of the metal tungsten (e.g., $WO_4^{2-}$), could be used to block anaerobic respiration, thereby reducing or ending the bloom of Enterobacteriaceae and serving as a treatment for flares of IBD. Tungsten can substitute as a competitive antagonist for molybdenum in the molybdopterin cofactor of bacterial respiratory reductases, thereby preventing nitrate respiration, DMSO respiration and TMAO respiration for nitrate, DMSO and TMAO (Takahashi et al., *Biochimica et biophysica acta*, 23:433-5 (1957)).

As described in Example 2, tungstate treatment prevented growth of Enterobacteriaceae by blocking anaerobic respiration in vivo and reduced morbidity in an IBD model. DSS-treated mice were provided regular drinking water or drinking water containing 2 g/l sodium tungstate ($Na_2WO_4 \times 2H_2O$) to receive a calculated average dose of 130 mg/kg/day (assuming 2.6 ml of water intake per day for each animal). To determine whether Enterobacteriaceae could grow by anaerobic respiration, these mice were then inoculated with an equal mixture of two *E. coli* indicator strains (wild-type and moaA mutant). In DSS-treated mice receiving regular water, wild-type *E. coli* was recovered in significantly higher numbers than the moaA mutant, indicating that anaerobic respiration supported bacterial growth in this particular environment. In contrast, tungstate treatment significantly reduced numbers of *E. coli* recovered from the intestine and abrogated the growth advantage of the wild-type over the moaA mutant. Furthermore, DSS-treated mice receiving regular drinking water exhibited increased morbidity compared to tungstate-treated mice, as indicated by measuring weight loss. As such, these data establish that inhibition of anaerobic respiration by tungstate treatment is capable of restoring a normal microbial community structure in the distal gut and reduce morbidity during IBD. These data also demonstrate that tungstate reduces intestinal inflammation through a microbiota-dependent mechanism.

Although antibiotic treatment may be beneficial in some cases during flares of IBD, such therapy targets Clostridia, Bacteroidia, and Enterobacteriaceae alike. In contrast, tungstate treatment only inhibits growth of Enterobacteriaceae, while leaving Clostridia and Bacteroidia unharmed. In other words, while antibiotic therapy kills both beneficial and harmful bacteria, tungstate treatment would target only the harmful bacteria, thereby restoring a normal bacterial community structure. As a result, the present invention represents a novel treatment concept that has the advantage that colonization resistance mediated by the normal gut microbiota (i.e., Bacteroidia and Clostridia) would not be eliminated, while the relative abundance of potentially harmful bacteria (e.g., Enterobacteriaceae) would be reduced and/or restored to its normal amount as observed in non-inflamed intestine. Thus, in certain aspects, the present invention provides methods for treating dysbiosis in a subject having gastrointestinal inflammation such as IBD by administering a tungstate salt to the subject in an amount sufficient to inhibit the activity of one or more anaerobic respiratory enzymes in Enterobacteriaceae.

II. Definitions

As used herein, the following terms have the meanings ascribed to them unless specified otherwise.

The term "gastrointestinal inflammation" includes a disorder/disease condition that causes or is associated with inflammation and/or ulceration in the mucous membrane of the gastrointestinal tract, such as, for example, the upper gastrointestinal tract (e.g., esophagus, stomach, and/or duodenum), the lower gastrointestinal tract (e.g., bowel such as small and/or large intestines), and/or the anus.

The term "inflammatory bowel disease" or "IBD" is used interchangeably herein to include diseases of the bowel (e.g., gut) that cause inflammation and/or ulceration and includes without limitation Crohn's disease, ulcerative colitis, and indeterminate colitis.

The term "Crohn's disease" or "CD" includes a type of IBD that can affect any part of the bowel, e.g., from mouth to anus. A feature of Crohn's disease is the granular, reddish-purple edematous (swollen) thickening of the bowel wall. Crohn's disease can be continuous or relapsing, mild or severe. Typically, Crohn's disease is not curable by resection of the involved segment of bowel. Most patients with Crohn's disease require surgery at some point, but subsequent relapse is common and continuous medical treatment is usual.

The term "ulcerative colitis" or "UC" includes a type of IBD that afflicts the large intestine. The course of the disease can be continuous or relapsing, mild or severe. Symptoms of the disease include cramping, lower abdominal pain, rectal bleeding, and frequent, loose discharges consisting mainly of blood, pus and mucus with scanty fecal particles. A total colectomy may be required for acute, severe or chronic, unremitting ulcerative colitis. The clinical features of UC are highly variable, and the onset may be insidious or abrupt, and may include diarrhea, tenesmus and relapsing rectal bleeding. Extraintestinal manifestations include arthritis, pyoderma gangrenoum, uveitis, and erythema nodosum.

The term "indeterminate colitis" or "IC" includes a type of IBD separate from Crohn's disease or ulcerative colitis wherein no specific features, characteristics, and/or pathology for either Crohn's disease or ulcerative colitis are detected. The term is used to describe patients in whom a diagnosis of UC or CD cannot be made based on standard clinical testing, including colonoscopy, imaging, laboratory tests, and biopsy.

The term "dysbiosis" includes a condition of microbial (e.g., bacterial, yeast, viral, parasite, etc.) imbalance within the body, such as when the symbiosis of the gut microbiota is dysregulated or disrupted. As a non-limiting example, an overgrowth of Enterobacteriaceae can cause dysbiosis.

The term "colitis" includes inflammation of the colon (e.g., large intestine).

The term "HIV enteropathy" includes a gastrointestinal dysfunction (e.g., a change in gastrointestinal structure and/or function) due to a human immunodeficiency virus (HIV) infection (see, e.g., Downs, *S. Afr. Clin. Nutr.*, 23, S65-68 (2010)). HIV enteropathy can be characterized by diarrhea, increased gastrointestinal inflammation, increased intestinal permeability, and/or malabsorption of bile acids and vitamin B12.

A "therapeutically effective amount" includes an amount or quantity effective, at dosages and for periods of time necessary, to achieve the desired therapeutic or prophylactic result.

The term "Enterobacteriaceae" includes members of a family of gram-negative bacteria, such as, but not limited to, *Escherichia, Enterobacter, Erwinia, Klebsiella, Pantoea, Photorhabdus, Providencia, Salmonella, Serratia, Shigella, Morganella Yersinia*, and the like. In particular embodiments, the term includes those classified into the Enterobacteriaceae family according to the taxonomy used by the NCBI (National Center for Biotechnology Information) database.

The term "tungstate salt" includes a salt of tungstate, wherein tungstate contains an oxoanion or a mixed oxide of tungsten and the cation moiety of the salt includes, but is not limited to, sodium, potassium, magnesium, and calcium cations. Non-limiting examples of tungstate ions include $HWO_4^-$ (hydrogentungstate), polymeric $W_2O_7^{2-}$ ions (e.g., in $Na_2W_2O_7$, $Li_2W_2O_7$ and $Ag_2W_2O_7$), $[W_7O_{24}]^{6-}$ (paratungstate A), $[W_{10}O_{32}]^{4-}$ (tungstate Y), $[H_2W_{12}O_{42}]^{10-}$ (paratungstate B), $\alpha\text{-}[H_2W_{12}O_{40}]^{6-}$ (metatungstate), $\beta\text{-}[H_2W_{12}O_{40}]^{6-}$ (tungstate X), and mixtures thereof.

The term "subject" or "patient" or "individual" typically includes humans, but can also include other animals such as, e.g., other primates, rodents, canines, felines, equines, ovines, porcines, and the like.

III. Detailed Description of the Embodiments

In certain aspects, the methods of the present invention for treating and/or preventing dysbiosis (e.g., microbial imbalance) in a subject having or suspected of having gastrointestinal inflammation comprises administering a therapeutically effective amount of an inhibitor of nitrate, DMSO, and TMAO respiration to the subject (e.g., a human patient). In certain embodiments, the inhibitor of nitrate, DMSO, and TMAO respiration comprises a soluble tungstate salt.

In some embodiments, the methods provided herein can be used for treating and/or preventing a disease or disorder associated with gastrointestinal inflammation. Examples of such diseases or disorders include, but are not limited to, inflammatory bowel disease (e.g., Crohn's disease, ulcerative colitis, indeterminate colitis), HIV enteropathy, colitis, necrotizing enterocolitis (NEC), colon cancer, colitis-associated colon cancer, chronic fatigue syndrome, leaky gut syndrome, nutrient-induced inflammation, cystic fibrosis, bacterial gastroenteritis, celiac disease, systemic lupus erythematosus, and the like.

Non-limiting examples of tungstate salts useful in the present invention include sodium tungstate, sodium tungstate dehydrate, chloride tungstate, magnesium tungstate, oxychloride tungstate, potassium tungstate, polyoxotungstates, tungstophosphoric acid, alanine complex of tungstophosphoric acid, tungstic acid, tungstoantimonic acid, tungstosilicic acid hydrate, tungsten trioxide, ammonium 21-tungsto-9-antimonate, tetrathiotungstate, and mixtures thereof.

Tungstate salts are commercially available from, for example, Sigma-Aldrich, St. Louis, Mo.; Santa Cruz Biotechnology, Santa Cruz, Calif.; and Thermo Fisher Scientific, Waltham, Mass.

In some embodiments, the methods of the present invention reduce the abundance of Enterobacteriaceae in a subject having or suspected of having gastrointestinal inflammation. In particular embodiments, the methods of the present invention reduce gastrointestinal inflammation in a subject in need thereof, e.g., by reducing the abundance of Enterobacteriaceae in the subject's gastrointestinal tract. In certain instances, the methods comprise administering a therapeutically effective amount of an inhibitor of nitrate, DMSO, and TMAO respiration to the subject (e.g., a human patient) capable of reducing the abundance (e.g., level or amount) of Enterobacteriaceae present in the subject's gastrointestinal tract. In particular embodiments, the inhibitor of nitrate, DMSO, and TMAO respiration comprises a soluble tungstate salt, as described herein.

In other embodiments, the therapeutically effective amount of the inhibitor (e.g., a tungstate salt) reduces the abundance (e.g., level or amount) of the Enterobacteriaceae in the subject's gut by at least about 50% compared to a control, e.g., at least about 50%, 55%, 60%, 65%, 70%, 75%, 80%, 85%, 90%, 91%, 92%, 93%, 94%, 95%, 96%, 97%, 98%, 99%, or 100%. In some embodiments, the tungstate salt reduces the abundance (e.g., level or amount) of the Enterobacteriaceae in the subject's gut by at least about 80% compared to a control. In some embodiments, the control comprises a sample from the subject or a similar subject taken prior to receiving the therapeutic agent, e.g., tungstate salt. In certain embodiments, the therapeutically effective amount of the inhibitor (e.g., a tungstate salt) restores (e.g., by decreasing or reducing) the abundance (e.g., level or amount) of the Enterobacteriaceae in the subject's gut to its normal amount as observed in non-inflamed intestine of a healthy subject (e.g., a subject not having or suspected of having gastrointestinal inflammation). In particular embodiments, the methods of the present invention restore a normal microbial community in the gastrointestinal tract (e.g., distal gut) of the subject, e.g., by decreasing the relative abundance of facultative anaerobic bacteria such as Enterobacteriaceae compared to the relative abundance of obligate anaerobic bacteria such as Bacteroidia and Clostridia.

Methods that can be used to determine, measure, or detect the abundance (e.g., level or amount) of a bacteria such as Enterobacteriaceae in a subject's sample (e.g., stool, serum or gastrointestinal tissue sample) include, but are not limited to, selective culture-based analysis (e.g., culturing on differential media for bacterial selection), non-selective culture-based analysis, microscopic analysis (e.g., histopathology), enzyme or metabolite analysis, immunoassay (e.g., ELISA, solid phase immunoassay, Western blot, protein microarray), electrophoretic analysis, restriction length polymorphism analysis, sequence analysis, hybridization analysis, ribotyping analysis, ribosomal DNA heterogeneity analysis, and PCR analysis (e.g., quantitative PCR (qPCR), quantitative real-time PCR (qRT-PCR), PCR-based denaturing-gradient-gel-electrophoresis (PCR-DGGE), repetitive extragenic palindromic-PCR (rep-PCR) and/or enterobacterial repetitive intergenic consensus PCR (ERIC-PCR)). Detailed descriptions of methods useful to the present invention are found in, for example, Inglis et al., *J. AOAC Int.*, 95(1):5-23 (2012) and O'Sullivan, D J., *Curr. Issues Intest. Microbial.*, 1(2):39-50 (2000). These assays have been well-described and standard methods are known in the art. See, e.g., Ausubel et al., *Current Protocols in Molecular Biology*, John Wiley & Sons, Inc. New York (1984-2008), Chapter 7 and Supplement 47; Theophilus et al., "PCR Mutation Detection Protocols," Humana Press, (2002); Innis et al., *PCR Protocols*, San Diego, Academic Press, Inc. (1990); Maniatis et al., *Molecular Cloning: A Laboratory Manual*, Cold Spring Harbor Lab., New York, (1982); Ausubel et al., *Current Protocols in Genetics and Genomics*, John Wiley & Sons, Inc. New York (1984-2008); and Ausubel et al., *Current Protocols in Human Genetics*, John Wiley & Sons, Inc. New York (1984-2008); all incorporated herein by reference in their entirety for all purposes.

In other aspects, the present invention provides methods for treating and/or preventing dysbiosis (e.g., microbial imbalance) in a subject having gastrointestinal inflammation such as IBD comprising administering a therapeutically effective amount of an iNOS inhibitor, a ROS inhibitor, or a combination thereof to the subject.

In some embodiments, the methods described herein for reducing the abundance (e.g., level or amount) of the Enterobacteriaceae in a subject (e.g., a human) having or suspected of having gastrointestinal inflammation includes administering a therapeutically effective amount of an iNOS inhibitor, a ROS inhibitor, or a combination thereof to the subject to decrease the abundance of Enterobacteriaceae in the subject's gut.

Non-limiting examples of iNOS inhibitors include aminoguanidine (AG); $N^G$-nitro-L-arginine; $N^G$-monomethyl-L-arginine; $N^G$-(1-iminoethyl)-L-lysine; $N^G$-nitro-L-arginine; S-methyl-L-thiocitrulline; $N^G$-monomethyl-L-arginine acetate; diphenyleneiodonium chloride; isothiourea derivatives; monomethyl-L-arginine acetate; 2-iminopiperidine; 2,4-diamino-6-hydroxy-pyrimidine; L-N-iminoethyl-lysine; 5-chloro-1,3-dihydro-2H-benzimidazol-2-one (FR038251); 1,-3(2H,4H)-isoquinoline-dione (FR038470); 5-chloro-2,4 (1H,3H)-quinazolonedione (FR191863); GW274150; 7-amino-3,4,5,6,tetrahydro-2H-azepin-2-yl-substituted imidazopyridine derivatives; pharmaceutically active derivatives thereof; pharmaceutically acceptable salts thereof; and mixtures thereof.

Non-limiting examples of ROS inhibitors include N-acetylcysteine (NAC), acetohydrazide, vitamins C, A and E, beta-carotene, allopurinol, carvediol, coenzyme Q, and mixtures thereof.

IV. Therapeutic Administration

A. Pharmaceutical Compositions

Compounds of the present invention are useful in the manufacture of a pharmaceutical composition or a medicament. In certain aspects, a pharmaceutical composition or medicament can be administered to a subject for the treatment of gastrointestinal inflammation including IBD (e.g., CD, UC, and IC), HIV enteropathy, colitis, and the like.

Pharmaceutical compositions or medicaments for use in the present invention can be formulated by standard techniques using one or more physiologically acceptable carriers or excipients. Suitable pharmaceutical carriers are described herein and in, e.g., "Remington's Pharmaceutical Sciences" by E. W. Martin. Compounds and agents of the present invention and their physiologically acceptable salts and solvates can be formulated for administration by any suitable route, including, but not limited to, orally, topically, nasally, rectally, parenterally (e.g., intravenously, subcutaneously, intramuscularly, etc.), and combinations thereof. In preferred embodiments, the pharmaceutical composition is administered orally. In some embodiments, the therapeutic agent is dissolved in a liquid, for example, water.

For oral administration, a pharmaceutical composition or a medicament can take the form of, e.g., a tablet or a capsule prepared by conventional means with a pharmaceutically acceptable excipient. Preferred are tablets and gelatin capsules comprising the active ingredient, i.e., a tungstate salt, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, anhydrous colloidal silica, talcum, stearic acid, its magnesium or calcium salt (e.g., magnesium stearate or calcium stearate), metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulfate, and/or (f) absorbents, colorants, flavors and sweeteners. In some embodiments, the tablet contains a mixture of hydroxypropyl methylcellulose, polyethyleneglycol 6000 and titatium dioxide. vTablets may be either film coated or enteric coated according to methods known in the art.

Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

In some embodiments, the therapeutic agent is prepared with a polysaccharide such as chitosan or derivatives thereof (e.g., chitosan succinate, chitosan phthalate, etc.), pectin and derivatives thereof (e.g., amidated pectin, calcium pectinate, etc.), chondroitin and derivatives thereof (e.g., chondroitin sulfate), and alginates.

In some embodiments, the therapeutic agent provided herein is loaded onto polymeric nanoparticles that can target the site of inflammation. Examples of nanoparticles include biodegradable nanoparticles, pH-sensitive nanoparticles (e.g., comprising Eudragit® S100), trimethylchitosan nanoparticles, polymeric nanoparticles (e.g., comprising PLGA, PEG-PLGA and/or PEG-PCL), and mannose-grafted polymeric nanoparticles. See, e.g., Coco et al., Int. J. Pharm. 440:3-12 (2013).

The therapeutic agent can be encapsulated in a controlled drug-delivery system such as a pressure controlled delivery capsule (see, e.g., Takaya et al., *J. Control Rel.*, 50:111-122 (1998)), a colon targeted delivery system, a osmotic controlled drug delivery system, and the like. The pressure controlled delivery capsule can contain an ethylcellulose membrane. The colon target delivery system can contain a tablet core containing lactulose which is over coated with an acid soluble material, e.g., Eudragit E®, and then overcoated with an enteric material, e.g., Eudragit L®. The osmotic controlled drug delivery system can be a single or more osmotic unit encapsulated with a hard gelatin capsule (e.g., capsule osmotic pump; commercially available from, e.g., Alzet, Cupertino, Calif.). Typically, the osmotic unit contains an osmotic push layer and a drug layer, both surrounded by a semipermeable membrane.

Typical formulations for topical administration include creams, ointments, sprays, lotions, and patches. The pharmaceutical composition can, however, be formulated for any type of administration, e.g., intradermal, subdermal, intravenous, intramuscular, intranasal, intracerebral, intratracheal, intraarterial, intraperitoneal, intravesical, intrapleural, intracoronary or intratumoral injection, with a syringe or other devices. Formulation for administration by inhalation (e.g., aerosol), or for oral, rectal, or vaginal administration is also contemplated.

The therapeutic agent can also be formulated in rectal compositions, for example, suppositories or retention enemas, for example, containing conventional suppository bases, for example, cocoa butter or other glycerides.

In certain embodiments, the pharmaceutical composition or medicament of the present invention comprises (i) an effective amount of a compound (e.g., one or more tungstate salts) as described herein, and optionally (ii) another therapeutic agent. When used with a compound of the present invention, such optional therapeutic agent may be used individually, sequentially, or in combination with one or more other such therapeutic agents (e.g., a first therapeutic agent, a second therapeutic agent, and a compound of the present invention). Administration may be by the same or different route of administration or together in the same pharmaceutical formulation.

In some embodiments, the pharmaceutical formulation of the tungstate salt for any therapeutic application (e.g., oral, topical, etc.) comprises about 0.05% to about 20% tungstate salt, e.g., about 0.05%, 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1.0%, 1.1%, 1.2%, 1.3%, 1.4%, 1.5%, 1.6%, 1.7%, 1.8%, 1.9%, 2.0%, 3%, 4%, 5%, 6%, 7%, 8%, 9%, 10%, 11%, 12%, 13%, 14%, 15%, 16%, 17%, 18%, 19%, or 20% tungstate salt. In some embodiments, the pharmaceutical formulation of the tungstate salt comprises about 0.05% to about 10% tungstate salt, e.g., about 0.05%, 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1.0%, 1.1%, 1.2%, 1.3%, 1.4%, 1.5%, 1.6%, 1.7%, 1.8%, 1.9%, 2.0%, 3%, 4%, 5%, 6%, 7%, 8%, 9%, or 10% tungstate salt. In other embodiments, the pharmaceutical formulation of the tungstate salt comprises about 0.05% to about 5% tungstate salt, e.g., about 0.05%, 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1.0%, 1.1%, 1.2%, 1.3%, 1.4%, 1.5%, 1.6%, 1.7%, 1.8%, 1.9%, 2.0%, 2.5%, 3%, 3.5%, 4%, 4.5%, or 5% tungstate salt. In yet other embodiments, the pharmaceutical formulation of the tungstate salt comprises about 0.01% to about 0.50% tungstate salt, e.g., e.g., about 0.01%, 0.02%, 0.03%, 0.04%, 0.05%, 0.06%, 0.07%, 0.08%, 0.09%, 0.10%, 0.11%, 0.12%, 0.13%, 0.14%, 0.15%, 0.16%, 0.17%, 0.18%, 0.19%, 0.20%, 0.21%, 0.22%, 0.23%, 0.24%, 0.25%, 0.26%, 0.27%, 0.28%, 0.29%, 0.30%, 0.35%, 0.40%, 0.45%, or 0.50% tungstate salt. In one embodiment, the pharmaceutical formulation of the tungstate salt comprises about 0.2% tungstate salt. In particular embodiments, the pharmaceutical formulation of the tungstate salt comprises about 0.2% sodium tungstate.

In some embodiments, the amount of the tungstate salt present in the pharmaceutical formulation is expressed as a weight by volume (w/v) percent or as a mass by volume (m/v) percent, e.g., based upon the total volume of the formulation. In other embodiments, the amount of the tungstate salt present in the pharmaceutical formulation is expressed as a weight by weight (w/w) percent, e.g., based upon the total weight of the formulation. In further embodiments, the amount of the tungstate salt present in the pharmaceutical formulation is expressed as a volume by volume percent (v/v), e.g., based upon the total volume of the pharmaceutical formulation. In particular embodiments, the pharmaceutical formulation of the invention comprises about 0.2% w/v of a tungstate salt.

B. Dosage

Pharmaceutical compositions or medicaments can be administered to a subject at a therapeutically effective dose to prevent, treat, reduce, or control gastrointestinal inflammation including IBD (e.g., CD, UC and IC), HIV enteropathy, colitis, and the like, as described herein. In some embodiments, the pharmaceutical composition or medicament is administered to a subject in an amount sufficient to elicit an effective therapeutic response in the subject.

The dosage of active agents administered is dependent on the subject's body weight, age, individual condition, surface area or volume of the area to be treated and on the form of administration. The size of the dose also will be determined by the existence, nature, and extent of any adverse effects that accompany the administration of a particular compound in a particular subject. A unit dosage for oral administration to an individual (e.g., human) of about 50 to 70 kg may contain between about 20 and 300 mg of the active ingredient. Typically, a dosage of the active compounds of the present invention is a dosage that is sufficient to achieve the desired effect. Optimal dosing schedules can be calculated from measurements of agent accumulation in the body of a subject. In general, dosage may be given once or more daily, weekly, or monthly. Persons of ordinary skill in the art can easily determine optimum dosages, dosing methodologies and repetition rates.

In some embodiments, the tungstate salt is administered at a dose (e.g., a daily dose) of about 10 mg to about 600 mg, e.g., about 10, 20, 30, 40, 50, 60, 70, 80, 90, 100, 150, 200, 250, 300, 350, 400, 450, 500, 550 or 600 mg. In other embodiments, the tungstate salt is administered at a dose (e.g., a daily dose) of about 25 mg to about 300 mg, e.g., about 25, 50, 75, 90, 100, 110, 120, 125, 130, 140, 150, 160, 170, 175, 180, 190, 200, 225, 250, 260, 275, 280, 290 or 300 mg. In particular embodiments, the daily dose of a tungstate salt such as sodium tungstate dihydrate is between about 0.5 mg to about 10 mg per kg weight, e.g., about 0.5 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg or 10 mg per kg weight.

In some embodiments, the tungstate salt is administered at about 15 mg to about 600 mg in a single dose a day. In some embodiments, the tungstate salt is administered at a dose of about 25 mg to about 300 mg twice a day, e.g., about 100 mg twice daily for a total of about 200 mg per day.

In some embodiments, the therapeutic agent is administered one or more times a day, e.g., 1, 2, 3, 4, 5, 6, 7, 8, 9, 10, or more times a day.

In some embodiments, the therapeutic agent is administered for about 1 to about 31 days, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. In some embodiments, the therapeutic agent is administered for at least 1 day. In other embodiments, the therapeutic agent is administered for one or more weeks, e.g., 1, 2, 3, 4, 5, 6, 7, 8, 9, 10, 11, 12, 13, 14, or more weeks. In yet other embodiments, the therapeutic agent is administered for one or more months, e.g., 1, 2, 3, 4, 5, 6, 7, 8, 9, 10, 11, 12, or more months.

To achieve the desired therapeutic effect, compounds or agents may be administered for multiple days at the therapeutically effective daily dose. Thus, therapeutically effective administration of compounds to treat a pertinent condition or disease described herein in a subject requires periodic (e.g., daily or twice daily) administration that continues for a period ranging from three days to two weeks or longer. While consecutive daily doses are a preferred route to achieve a therapeutically effective dose, a therapeutically beneficial effect can be achieved even if the agents are not administered daily, so long as the administration is repeated frequently enough to maintain a therapeutically effective concentration of the agents in the subject. For example, one can administer the agents every day, every other day, or, if higher dose ranges are employed and tolerated by the subject, twice a week.

Optimum dosages, toxicity, and therapeutic efficacy of such compounds or agents may vary depending on the relative potency of individual compounds or agents and can be determined by standard pharmaceutical procedures in experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Agents that exhibit large therapeutic indices are preferred. While agents that exhibit toxic side effects can be used, care should be taken to design a delivery system that targets such agents to the site of affected tissue to minimize potential damage to normal cells and, thereby, reduce side effects.

The data obtained from, for example, animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration.

A dose can be formulated in animal models to achieve a concentration range that includes the $IC_{50}$ (the concentration of the agent that achieves a half-maximal inhibition of symptoms) as determined in cell culture. Such information can be used to more accurately determine useful doses in humans. Levels in stool or an enteric tissue sample can be measured, for example, by high performance liquid chromatography (HPLC). In general, the dose equivalent of agents is from about 1 ng/kg to about 100 mg/kg for a typical subject.

The dosage of a pharmaceutical composition of the present invention can be monitored and adjusted throughout treatment, depending on severity of symptoms, frequency of recurrence, and/or the physiological response to the therapeutic regimen. Those of skill in the art commonly engage in such adjustments in therapeutic regimens.

V. Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

Anaerobic Respiration Controls Growth of Enterobacteriaceae in the Large Bowel During Host Inflammatory Response This example shows that terminal respiratory electron acceptors are generated as a byproduct of the host inflammatory response and increase the fitness of Enterobacteriaceae to efficiently outcompete obligate anaerobic bacteria, a process that can further exacerbate intestinal mucosa.

It has been shown that (i) reactive oxygen and nitrogen species are produced during intestinal inflammation generate respiratory electron acceptors, and (ii) electron acceptors are available in the inflamed gut to support growth of E. coli by anaerobic respiration, which is more efficient for energy production than fermentation. This example shows that anaerobic respiration is one of the fundamental principles that governs the phylum-level changes in the composition of gut-associated microbial communities during inflammation.

Introduction

*E. coli* possesses three nitrate reductases encoded by the narGHJI, narZYWV, and napFDAGHBC operons, two DMSO reductases encoded by the dmsABC and ynfFGH operons, and three TMAO reductases encoded by the torCAD, torYZ, and yedYZ operons (59). In *E. coli*, the respiratory reductases for nitrate, DMSO and TMAO as well as the formate dehydrogenases FdnG and FdoG contain molybdenum (Mo) as a key catalyst for electron transfer reactions. The functions of FdnG and FdoG are linked to respiration because these two formate dehydrogenases couple respiratory electron acceptors to the electron donor formate, a fermentation end product present in the large intestine. Formate dehydrogenases and respiratory reductases contain Mo within a molybdopterin cofactor. MoaA catalyzes the first reaction in the biosynthesis of this molybdopterin cofactor. Therefore, an *E. coli* moaA mutant is deficient for several respiratory pathways, including nitrate respiration, DMSO respiration and TMAO respiration. The cause and effect relationship between anaerobic respiration and commensal Enterobacteriaceae growth during colitis was pursued by using *E. coli* as a prototypical representative of this group.

Results

Figure 2:
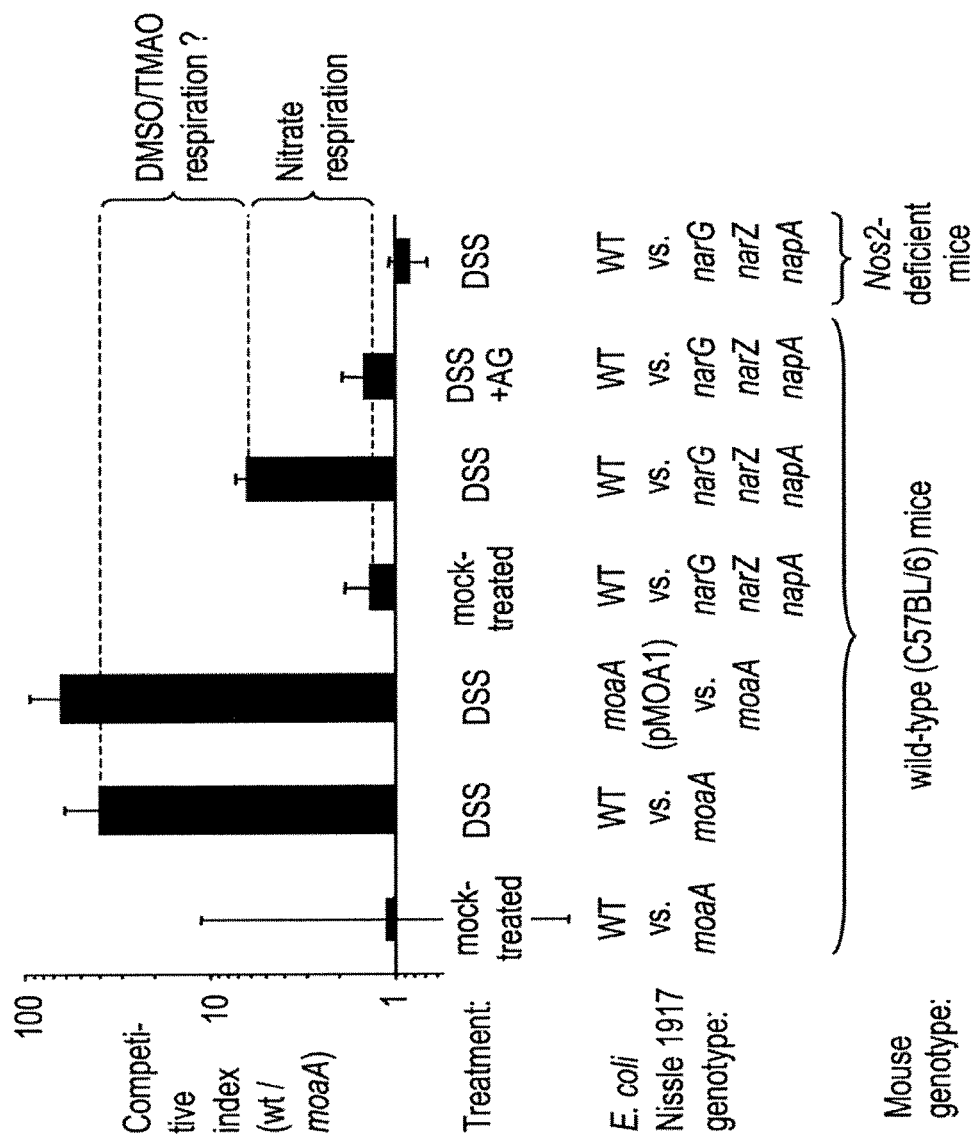
FIG. 2 shows that anaerobic respiration boosts growth of E. coli during colitis. Mice were mock-treated or treated with dextran sulfate sodium (DSS) or DSS+aminoguanidine (AG) and infected with equal mixtures of the indicated E. coli strains. Five days after infection, the ratio of wild-type (wt) and mutant recovered from colon contents was determined (competitive index). Bars represent geometric means±standard error.

1. Relationship Between Anaerobic Respiration and Growth of Commensal Enterobacteriaceae During Colitis To test whether anaerobic respiration confers a fitness advantage during colitis, DSS-treated mice were inoculated with an equal mixture of the commensal *E. coli* Nissle 1917 and its isogenic moaA mutant (competitive infection design). For comparison, mock-treated mice were inoculated with an equal mixture of both strains. Mock-treated mice did not develop colitis, were poorly colonized by the *E. coli* strain mixture and the wild type and moaA mutant were recovered in equal numbers five days after inoculation. In contrast, the *E. coli* Nissle 1917 wild type was recovered in markedly higher numbers than the moaA mutant from mice with dextran sulfate sodium (DSS)-induced colitis (FIG. 2). The moaA mutant could be complemented with a plasmid containing the cloned moaA gene (pMOA1) (FIG. 2). These data showed that nitrate respiration, DMSO respiration, and/or TMAO respiration contribute to the growth of *E. coli* in the inflamed intestine.

Figures 3A, 3B:
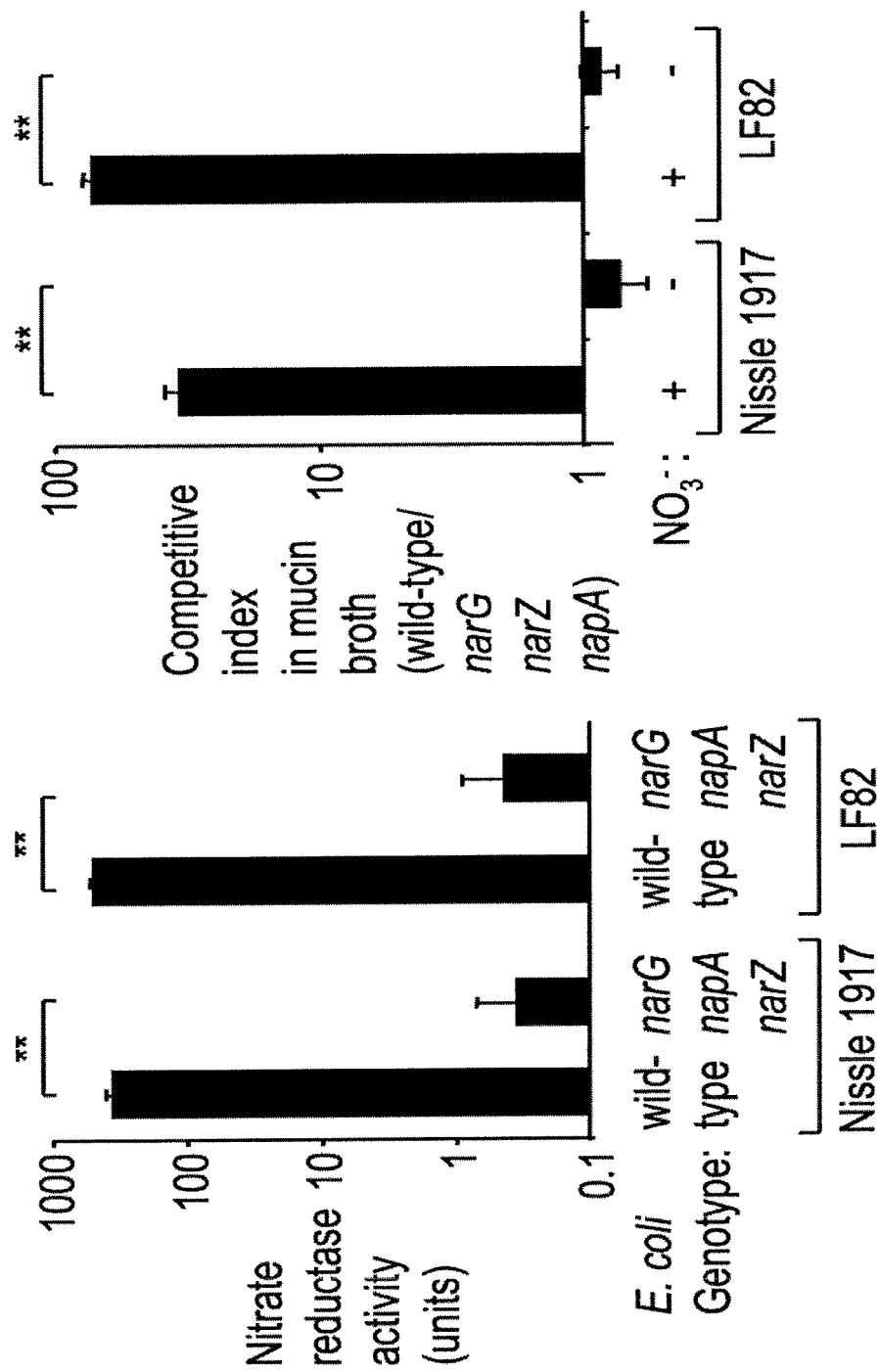
FIGS. 3A-B show characterization of nitrate respiration-deficient mutants.

Next, the contribution of individual electron acceptors was examined. It was determined whether nitrate respiration contributes to luminal growth of *E. coli* during colitis. A Nissle 1917 derivative carrying mutations in narG, napA and narZ, encoding the three nitrate reductases of E. coli was generated. The resulting narG napA narZ mutant did not exhibit nitrate reductase activity in an enzymatic assay (FIG. 3A). In the presence of nitrate, the wild type strain outcompeted the narG napA narZ mutant during anaerobic growth in mucin broth (FIG. 3B).

Next, mock-treated mice (C57BL/6) or mice with DSS-induced colitis were inoculated with an equal mixture of *E. coli* Nissle 1917 and its isogenic nitrate respiration-deficient mutant (competitive infection design). Wild type and nitrate respiration-deficient mutant strains colonized the intestine of normal mice poorly, but similar numbers of each strain were recovered from colon contents (FIG. 2). The data suggested that nitrate respiration provides no growth benefit in the absence of intestinal inflammation. In contrast, *E. coli* Nissle 1917 robustly colonized the inflamed intestine of DSS-treated mice and the respiration-deficient mutant strain was recovered in significantly lower numbers ($P<0.05$) than its wild-type parent. Thus, nitrate respiration enhanced the fitness of *E. coli* in the inflamed gut.

Figure 4:
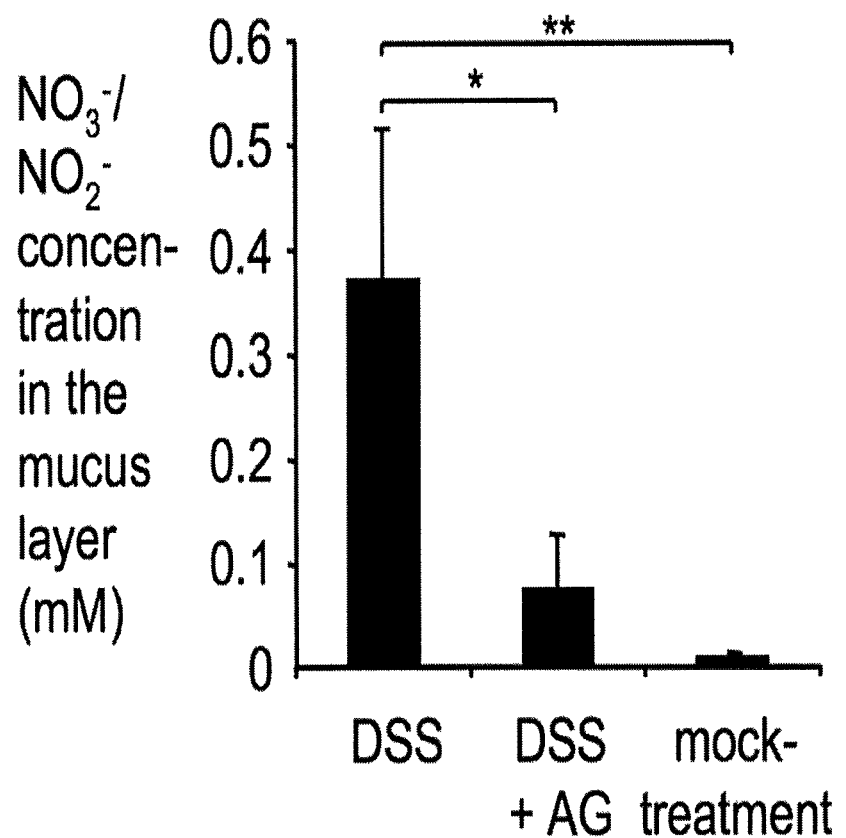
FIG. 4 shows nitrate/nitrite concentration in the cecal mucus of mock-treated mice or mice treated with DSS or DSS+AG. Bars represent geometric means±standard error. *, $P<0.05$; **, $P<0.01$.

To determine whether the availability of nitrate increases during DSS colitis, the concentration of nitrate/nitrite in the colonic mucus of mock-treated and DSS-treated mice was examined. A marked increase in the concentration of nitrate/nitrite was observed in mice with DSS colitis (FIG. 4). The results supported the idea that the inflammatory host response generates respiratory electron acceptors in the large bowel.

To determine whether growth of *E. coli* was boosted by dietary nitrate or host-derived nitrate, mice carrying a mutation in the Nos2 gene, encoding iNOS, were treated with DSS and inoculated with an equal mixture of *E. coli* Nissle 1917 and its isogenic nitrate respiration-deficient mutant (narG napA narZ mutant). Remarkably, the *E. coli* Nissle 1917 parent and its nitrate respiration-deficient mutant were recovered in equal numbers from Nos2-deficient mice (FIG. 2). The data indicated that nitrate driving anaerobic respiration of *E. coli* in the inflamed gut was host-derived.

2. Contribution of Anaerobic Respiration to Growth of Adherent-invasive *Escherichia Coli* (AIEC) During Colitis One of the possible consequences of dysbiosis is an exacerbation of pre-existing inflammatory conditions. It is well established that the presence of gut microbes is a prerequisite for the development of chronic intestinal inflammation in genetically predisposed mice (48, 54). However, recent studies suggest that a bloom of Enterobacteriaceae can be associated with enhanced intestinal inflammation. For example, in a mouse model of ulcerative colitis, changes in the microbial community structure characterized by an increased luminal abundance of Enterobacteriaceae can be transferred to other animals, resulting in an exacerbation of intestinal inflammation (20, 21). Adherent-invasive Escherichia coli (AIEC) are isolated more commonly from the intestinal mucosa of individuals with Crohn's disease than from healthy controls (9, 10). AIEC colonize and exacerbate gut inflammation in mice with dextran sulfate sodium (DSS)-injured colon (7). Thus, an inflammation-induced bloom of Enterobactericeae potentially can have adverse consequences, particularly if the microbiota contains more harmful members of this group, such as AIEC.

Figure 5:
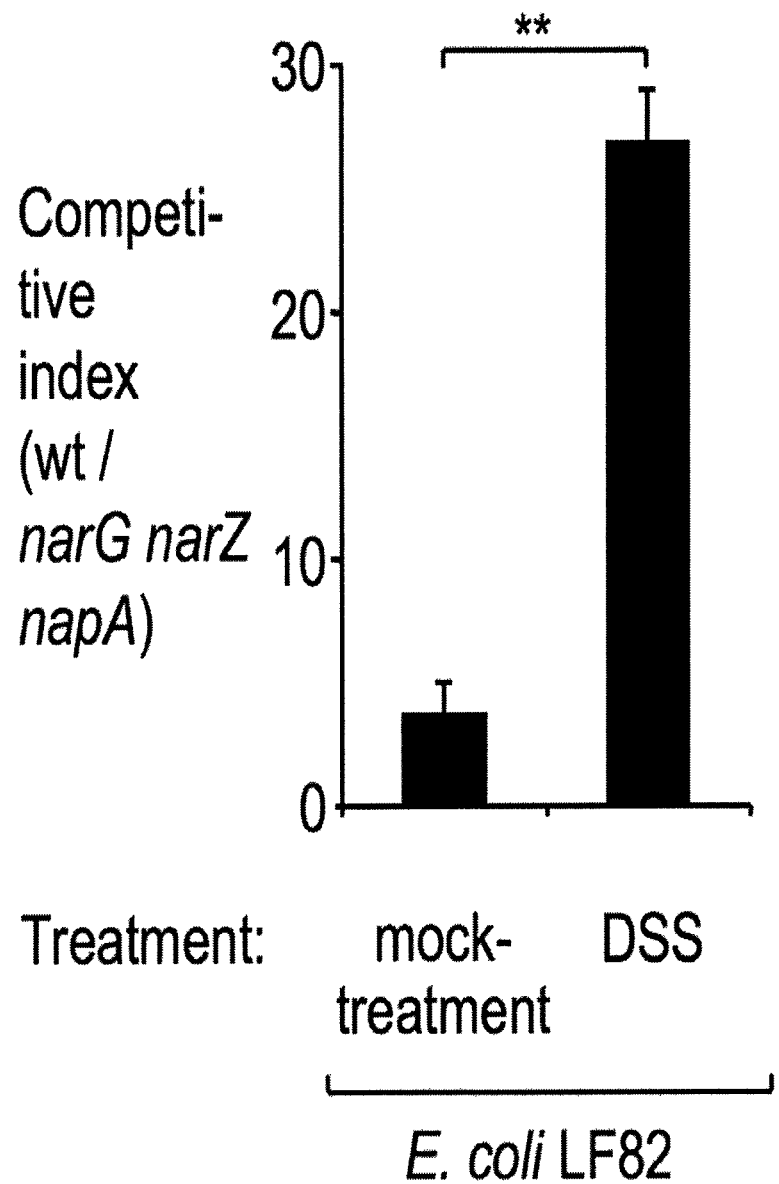
FIG. 5 shows that nitrate respiration enhances luminal growth of E. coli LF82 during inflammation. Mice were mock-treated or treated with DSS and infected with an equal mixture of LF82 (wt) and a narG narZ napA mutant. Five days after infection, the competitive index was determined. Bars represent geometric means±standard error. **, $P<0.01$.

The data described above in the previous section demonstrates that gut inflammation generates electron acceptors that boost luminal growth of commensal E. coli by anaerobic respiration. To test whether nitrate respiration contributes to luminal growth of AIEC strain LF82 in DSS-treated mice, a nitrate respiration-deficient mutant (narG napA narZ mutant) of LF82 was generated (FIG. 3). Mock-treated mice (C57BL/6) or mice with DSS-induced colitis were inoculated with an equal mixture of LF82 and its isogenic nitrate respiration-deficient mutant (competitive infection design). The LF82 wild type and the LF82 narG napA narZ mutant were recovered in similar numbers from colon contents of mock-treated mice (FIG. 5). In contrast, the LF82 narG napA narZ mutant was recovered in significantly (P<0.01) lower numbers than the LF82 wild type from DSS-treated mice. Thus, nitrate respiration enhances luminal growth of LF82 during DSS-induced colitis, but not in the absence of intestinal inflammation.

The competitive advantage of the E. coli Nissle 1917 wild type over the moaA mutant was significantly (P<0.05) greater than that over the nitrate respiration-deficient mutant (narG napA narZ mutant) (FIG. 2). These data support the idea that in addition to nitrate respiration, DMSO respiration and/or TMAO respiration contribute to growth of E. coli in the inflamed intestine.

3. Analysis of Treatments for Intestinal Inflammation

The data show that nitrate is a by-product of colitis (FIG. 4) which enhances growth of AIEC by nitrate respiration (FIG. 5). Since the fitness advantage conferred by nitrate respiration was abrogated in Nos2-deficent mice (FIG. 2), the ability of inhibiting nitrate respiration in vivo was tested by supplementing the drinking water of mice with the iNOS inhibitor aminoguanidine (AG). Remarkably, AG treatment markedly reduced the availability of nitrate/nitrite in the large bowel of DSS-treated mice (FIG. 4) and abrogated the fitness advantage conferred by nitrate respiration (FIG. 2). The data shows that it is possible to block the generation of respiratory electron acceptors by inhibiting the formation of radicals during colitis.

In addition to blocking RNS production with AG, preventing the generation of ROS with N-acetylcysteine (NAC) was tested. The oxygen radical scavenger NAC has been shown to suppress the oxidative burst activity of neutrophils in vivo (33) and can almost completely inhibit the oxidative response of neutrophils to E. coli at a concentration of 76 mM in vitro (8, 44). In these experiments, mice are fed chow supplemented with NAC (4 mg NAC/100 g chow). Assuming an average consumption of 5 g chow/day for a small mouse, this regimen provides a daily dose of approximately 0.2 mg NAC, which corresponds to the daily oral dose (600 mg/60 kg weight) that has been administered successfully in humans to treat tissue damage from inflammatory disorders (49).

Finally, tungstate (an oxide of the metal tungsten [e.g., $WO_4^{2-}$]), which substitutes for molybdenum (Mo) in the molybdopterin cofactor as a competitive antagonist (61) was tested, thereby preventing nitrate respiration, DMSO respiration and TMAO respiration. Oral tungstate administration (100 mg twice a day for 6 weeks) has been tested in human clinical trials to treat obesity. While the treatment did not reduce body weight, it was not associated with abnormal safety parameters (27). In this experiment (see, e.g., Example 2 for further details), mice were provided drinking water containing 2 g/l sodium tungstate ($Na_2WO_4 \times 2H_2O$; Sigma-Aldrich, St. Louis, Mo., USA) to receive a calculated average dose of 130 mg/kg/day (assuming 2.6 ml of water intake per day for each animal) (26).

Groups of 6 DSS-treated mice (C57BL/6) were provided with water or water supplemented with AG or tungstate and fed regular chow or chow supplemented with NAC. Mice were then inoculated with wild-type LF82 or sterile medium (mock-infection) and organs were collected at three, five and seven days after infection. The development of intestinal inflammation was evaluated as described in Section 5 below.

Based on the data, LF82 exacerbated colitis in DSS-treated mice. However, AG+NAC treatment of mice infected with LF82 reduced inflammation and morbidity to levels (or below levels) of mock-infected DSS-treated mice. Treatment of mice with only one compound (i.e., with either AG or NAC) produced an intermediate effect. Tungstate inhibits all respiratory reductases containing a molybdopterin cofactor, thereby blocking nitrate respiration, DMSO respiration, and TMAO respiration. Thus, similar to inactivation of moaA (FIG. 2), tungstate-treatment led to a reduction in the growth of AIEC by anaerobic respiration, thereby reducing inflammation and morbidity.

4. Further Analysis of Anaerobic Respiration on the Growth of AIEC in Gastrointestinal Inflammation To further investigate the contribution of anaerobic respiration to the growth of AIEC in the inflamed intestine, the following experiments described below can be performed.

Mutants of AIEC reference strain LF82 carrying non-polar unmarked deletions in narG napA and narZ using suicide plasmid pRDH10, a suicide vector containing the sacB gene, which allows negative selection against vector sequences in the presence of sucrose, are generated. Additional mutants are generated, such as unmarked, non-polar deletions of the torA, torZ, dmsA, ynfF and yedY genes, each of which encode molybdopterin cofactor-containing reductase subunits. In brief, suicide plasmids are made for the construction of unmarked deletions by cloning the respective flanking DNA regions into pRDH10. The Shine-Dalgarno sequence of the respective downstream gene should be preserved. The resulting pRDH10 derivative are first inserted into the chromosome (e.g., single cross over) by selecting for its antibiotic resistance marker (e.g., tetracycline). Loss of pRDH10 from the chromosome (e.g., second cross over) are then selected for by growing the resulting strains in the presence of sucrose. Finally, colonies in which double-crossover events have resulted in an unmarked deletion of the gene encoding the respective reductase subunit are detected using PCR. Additional mutations are introduced into the LF82 narG napA narZ mutant, one by one, to produce a nitrate/DMSO/TMAO respiration-deficient mutant (narG napA narZ torA torZ dmsA ynfF yedY mutant). In addition, mutants that are deficient for all but one DMSO/TMAO reductase (e.g., a narG napA narZ torZ dmsA ynfF yedY mutant which is proficient for TorA, etc.) are also generated.

The growth benefit conferred by DMSO/TMAO respiration are assessed. In particular, competitive indices, similar to those of FIG. 3B, are generated of co-cultures of each of the resulting strains with wild-type LF83 in mucin broth under anaerobic conditions (e.g., anaerobe chamber) in the presence or absence of nitrate, S-oxides (e.g., DMSO or methionine-S-oxide) or N-oxides (e.g., TMAO, pyridine N-oxide or adenosine N-oxide).

In some instances, genes for complementation are chromosomally inserted into a neutral locus, the lac operon, which is not required for intestinal colonization once mice are weaned. For complementation, the gene encoding the respective reductase subunit is cloned behind its native promoter into a pRDH10 derivative carrying a fragment of lacZ cloned in opposite orientation. The resulting suicide plasmid is inserted via single crossover into the lac operon on the chromosome of the narG napA narZ torA torZ dmsA ynfF yedY mutant by selecting for its antibiotic resistance marker (tetracycline) and screening for loss of lactose utilization (i.e., white colonies on plates containing 5-bromo-4-chloro-3-indolyl-β-d-galactopyranoside [X-Gal]).

To investigate whether AIEC uses anaerobic respiration to exacerbate pathology, groups of 6 mock-treated mice (C57BL/6) or 6 mice with DSS-induced colitis are inoculated with a single $E.$ $coli$ strain (single infection design). Useful strains include the $E.$ $coli$ LF82 wild type strain, a nitrate/DMSO/TMAO respiration-deficient mutant (narG napA narZ torA torZ dmsA ynfF yedY mutant), a DMSO/TMAO respiration-deficient mutant (torA torZ dmsA ynfF yedY mutant), a nitrate respiration-deficient mutant (narG napA narZ mutant), selected complemented mutants (based on their phenotype determined by in vitro characterization) and a mock-inoculation control (sterile medium). Organs of the mice are harvested at five days after infection, a time point at which anaerobic respiration is needed to support a bloom of $E.$ $coli$ in DSS-treated mice (FIG. 2).

5. Further Analysis of the Development of Intestinal Inflammation

The development of intestinal inflammation can be followed as described below. The severity of inflammatory changes in the cecum and the colon are assessed by several independent approaches at three, five and seven days after inoculation. First, the relative transcript levels of genes encoding neutrophil chemoattractants (i.e., genes encoding the CXC-chemokines Kc and the Mip2) and iNOS (Nos2) are determined (see, e.g., 62, 64). Second, to monitor, on the protein level, how inflammatory markers increase after DSS treatment, expression levels of iNOS and myeloperoxidase (MPO) are analyzed in protein samples extracted from the colonic mucosa by Western blot using anti-iNOS antibodies (Abcam), anti-MPO antibodies (R&D systems), and anti-tubulin as a loading control (64). Third, concentrations of the neutrophil-specific enzyme MPO in fecal pellets are measured by ELISA. This can serve as an indicator for the degree of neutrophil transmigration into the intestinal lumen over time (6, 42). Finally, pathological changes in the colonic mucosa are assessed through standardized, blinded scoring of formalin-fixed, hematoxylin and eosin-stained sections by a veterinary pathologist (64).

In addition, colony forming units (CFU) of $E.$ $coli$ are determined by spreading homogenates of colon contents on plates containing the appropriate antibiotics (all LF82 derivatives are marked with a kanamycin resistance cassette inserted downstream of the lac operon). The composition of the cecal and colonic microbiota are interrogated using quantitative real-time PCR of 16S rRNA genes. See, (64). In some instances, DSS treatment is ended one day prior to collecting samples for the isolation of bacterial DNA from luminal contents because DSS can inhibit PCR analysis.

Inoculation of DSS-treated mice with AIEC can result in increased morbidity and greater severity of intestinal inflammation. In contrast, infection of mice with a nitrate/DMSO/TMAO respiration-deficient mutant of LF82 may not result in an exacerbation of colitis compared to mock-infected DSS-treated mice. Mutants deficient for only one pathway of anaerobic respiration are expected to display an intermediate phenotype.

6. Inflammation-dependent Anaerobic Respiration in Streptomycin Treated Mice

Figures 6A, 6B:
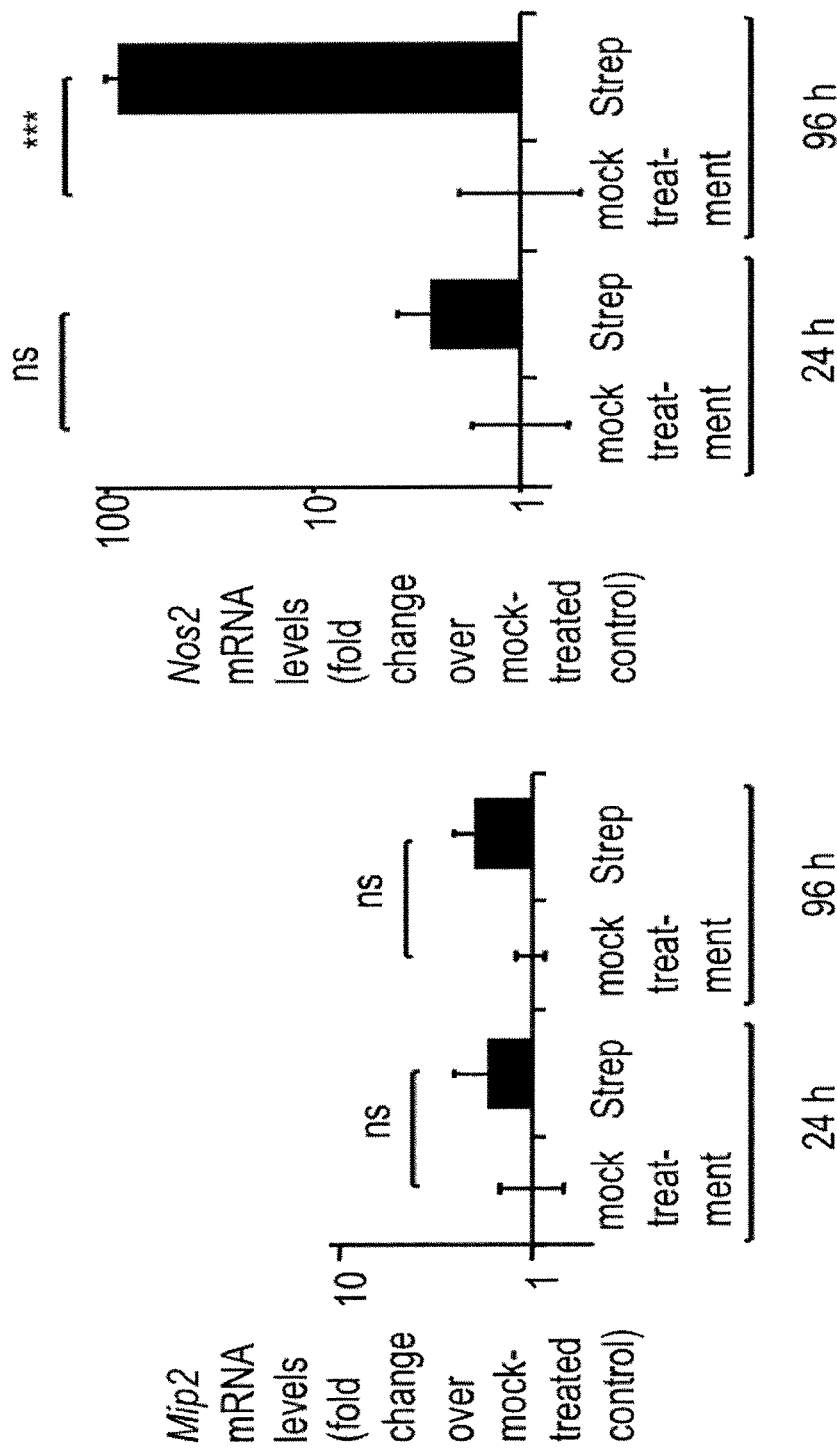
FIGS. 6A-B show the transcript levels of Mip2 (FIG. 6A) and Nos2 (FIG. 6B) in the cecal mucosa of mock-treated mice or streptomycin-treated mice as determined by quantitative real-time PCR at the indicated time points. Bars represent geometric means±standard error. ***, $P<0.001$; ns, not significantly different.

It has been reported that a bloom of Enterobacteriaceae arises following antibiotic treatment for colitis (57). For instance, streptomycin pre-treatment greatly enhances the ability of human $E.$ $coli$ isolates to colonize the mouse intestine. Interestingly, human $E.$ $coli$ isolates grow in the large bowel of streptomycin pre-treated mice using nitrate respiration (32). The effect of streptomycin treatment on gut physiology was analyzed to determine if anaerobic respiration is inflammation-dependent in this mouse model. Mice were treated with streptomycin (a single dose of 20 mg/mouse) or mock-treated and gene expression in the cecal mucosa was investigated over time by quantitative real-time PCR. The mRNA levels for Kc and Mip2, which encode neutrophil chemoattractants, were only modestly elevated after streptomycin treatment and this difference did not reach statistical significance (FIG. 6A). However, there was a marked increase in Nos2 transcript levels (encoding iNOS) four days after treatment of mice with streptomycin (FIG. 6B). This marked increase in Nos2 expression (in the absence of marked increases in other inflammatory markers) likely reflected infiltration of tissue with phagocytes expressing iNOS. To test this idea, flow cytometry analysis was performed to determine whether cellular infiltrates can be observed in response to streptomycin treatment. The gating strategy is shown in FIG. 7A. The analysis revealed that while no neutrophils were present in the cecal mucosa of mock-treated control animals, neutrophils ($CD3^-B220^-NK1.1^-CD11b^+Ly6C^+Ly6G^+$ cells) were present in streptomycin treated mice (FIG. 7B). Furthermore, streptomycin treatment was associated with an influx of inflammatory monocytes ($CD3^-B220^-NK1.1^-CD11b^+Ly6C^+Ly6G^-$ cells) (FIG. 7C). These data show that streptomycin treatment is associated with low-level inflammation. $E.$ $coli$ present in the gut of streptomycin treated mice relies on nitrate respiration which is likely associated with gut inflammation, iNOs expression, and/or nitrate production.

7. Further Analysis of the Restoration of Microbial Community Structure During Intestinal Inflammation Two different approaches can be used to induce intestinal inflammation and profile the resulting changes in gut-associated microbial communities. One approach includes the induction of colitis using DSS treatment. DSS treatment is accompanied by changes in the microbial community structure characterized by an increased relative abundance of facultative anaerobic Enterobacteriaceae (39). Experiments were performed in which DSS-treated mice were inoculated with an $E.$ $coli$ indicator strain. Analysis of 16S rRNA gene copy number by quantitative real-time PCR illustrated the considerable growth advantage conferred by DSS-induced colitis (FIG. 8). Instead of inoculating mice with $E.$ $coli$ indicator strains, the dynamics can be profiled in their endogenous microbial communities. To monitor dynamics within an animal over time, a hapten-induced colitis model (oxazolone-induced colitis) (5) can be used as a second approach and feces collected over time.

To investigate whether changes in the microbial communities that develop during inflammation are due to anaerobic respiration, the temporal dynamics of the entire gut community can be monitored in mouse models of colitis. In particular, colitis can be induced by DSS treatment or hapten-induced (oxazolone-treatment) in wild type and Nos2-deficient mice, including those that are additionally exposed to tungstate, AG, or NAC. The experiments can be performed as follows.

7a. DSS-induced Colitis Mouse Models

Wild type mice (C57BL/6) and Nos2-deficient mice are co-housed for two weeks to reduce the variation in the microbial community structure prior to inducing inflammation. Feces are collected from all animals for DNA isolation to establish a baseline of the microbiota composition at the beginning of the experiment. Six mice from each mouse strain (C57BL/6 mice or Nos2-deficient mice) are euthanized to isolate bacterial DNA from cecal and colon contents and to establish a baseline for inflammatory host responses using the methods described above (see, Section 5). Groups of mice from each mouse strain (e.g., C57BL/6 mice or Nos2-deficient mice) are treated with 4% DSS in drinking water or are "mock-treated" (i.e., mice will receive drinking water without DSS). Subsets of the DSS-treated group and the mock-treated group receives no supplementation in food or water (control group). Another subset of the groups receives water supplemented with AG and chow supplemented with NAC (AG+NAC treatment). And yet another subset of the groups receives water supplemented with tungstate (tungstate treatment). Fecal pellets are collected daily to follow the development of inflammation by measuring MPO levels (6, 42). At days 6 and 9 after the beginning of DSS treatment, members of the DS-treated group and the mock-treated group for each treatment regimen are euthanized to collected feces and organs. DSS treatment can be suspended one day prior to collection of organs.

The development of intestinal inflammation is monitored using methods described above (see, Section 5). Bacterial DNA is isolated from feces, colon contents and cecal contents and processed for next-generation sequencing analysis for analysis of 16S rRNA gene sequences to identify the microbiota of the mice.

7b. Oxazolone-induced Colitis Mouse Models

Six mice from each mouse strain (C57BL/6 mice or Nos2-deficient mice) are first lightly anesthetized with metofane (methoxyflurane; Pitman-Moore) and either 6 mg of the haptenating agent oxazolone (4-ethoxymethylene-2-phenyl-2-oxazolin-5-one, Sigma) is administered rectally in a volume of 0.15 ml in a 1:1 $H_2O$/ethanol mixture (50% ethanol) or a vehicle control (i.e. 0.15 ml of 50% ethanol) is administered by the same technique (mock treatment). As described above, groups of oxazolone-treated mice and mock-treated mice are used to form a control group, an AG+NAC treatment group and a tungstate treatment group, respectively. Feces is collected daily to isolate bacterial DNA and to measure MPO levels for following the development of inflammation (6, 42). Mice are euthanized 9 days after oxazolone treatment to collect organs for assessing intestinal inflammation (see, Section 5) and to isolate bacterial DNA from feces, colon contents and cecal contents and processed for next-generation sequencing (NGS) analysis for analysis of 16S rRNA gene sequences to identify the microbiota of the mice.

7c. Analysis of 16S rRNA Gene Sequences

For functional analysis of NGS data sets, software such as, but not limited to, PhyloSift (Darling et al., manuscript in preparation), NextGENe (Softgenetics, State College, Pa.), and Avadis NGS (Strand Scientific Intelligence, San Francisco, Calif.) is used. Principal component analysis is performed to test whether the total variation in the sample clusters individual mice together and whether or not these clusters reflect immune status (e.g., if communities from DSS-treated mice cluster with communities from oxazolone-treated mice) or whether the environment provides a possibility for anaerobic respiration (e.g., if communities from the AG+NAC treatment group cluster with communities collected from mice before inflammation was induced). Next, hierarchical clustering (using, for example, Euclidean, maximum, and minimum distance calculations), K-means clustering, and self-organizing-map clustering is performed to determine whether sample analysis cluster individual mice together. Finally, population stability (e.g., how much and how frequently a population changes) is examined through time to correlate changes with the development of host inflammatory responses or certain treatment regimens. To quantify stability, deviation from the difference between the maximum and minimum population levels is calculated to produce data on population variability.

Summary

In summary, this example demonstrates that the generation of electron acceptors that support nitrate, DMSO, and TMAO respiration is due to the host inflammatory response which then influences microbial growth in the gut. The human large intestine is host to a complex microbial community dominated by obligate anaerobic bacteria belonging to the phyla Bacteroidetes and Firmicutes. On the phylum level, this microbiota composition is highly conserved, not just between individuals but also between different mammalian species. However, conditions of intestinal inflammation can lead to a microbial imbalance (dysbiosis) characterized by a marked decrease in the representation of obligate anaerobic bacteria and an increased relative abundance of facultative anaerobic bacteria, such as Enterobacteriaceae. This example also describes mechanisms responsible for these phylum-level changes in the microbial community structure and how dysbiosis influences the resolution of inflammation. Moreover, the example shows that inhibition of anaerobic respiration by compounds such as tungstate can reestablish the microbial community in the inflamed gut.

References

1. Balagam, B., and D. E. Richardson. 2008. The mechanism of carbon dioxide catalysis in the hydrogen peroxide N-oxidation of amines. Inorganic chemistry 47:1173-8.
2. Barman, M., D. Unold, K. Shifley, E. Amir, K. Hung, N. Bos, and N. Salzman. 2008. Enteric salmonellosis disrupts the microbial ecology of the murine gastrointestinal tract. Infect Immun 76:907-15.
3. Baumgart, M., B. Dogan, M. Rishniw, G. Weitzman, B. Bosworth, R. Yantiss, R. H. Orsi, M. Wiedmann, P. McDonough, S. G. Kim, D. Berg, Y. Schukken, E. Scherl, and K. W. Simpson. 2007. Culture independent analysis of ileal mucosa reveals a selective increase in invasive Escherichia coli of novel phylogeny relative to depletion of Clostridiales in Crohn's disease involving the ileum. ISME J 1:403-18.
4. Berger, T., A. Togawa, G. S. Duncan, A. J. Elia, A. You-Ten, A. Wakeham, H. E. Fong, C. C. Cheung, and T. W. Mak. 2006. Lipocalin 2-deficient mice exhibit increased sensitivity to Escherichia coli infection but not to ischemia-reperfusion injury. Proc Natl Acad Sci USA 103:1834-9.
5. Boirivant, M., I. J. Fuss, A. Chu, and W. Strober. 1998. Oxazolone colitis: A murine model of T helper cell type 2 colitis treatable with antibodies to interleukin 4. The Journal of experimental medicine 188:1929-39.
6. Bradley, P. P., D. A. Priebat, R. D. Christensen, and G. Rothstein. 1982. Measurement of cutaneous inflammation: estimation of neutrophil content with an enzyme marker. J Invest Dermatol 78:206-9.
7. Carvalho, F. A., N. Barnich, P. Sauvanet, C. Darcha, A. Gelot, and A. Darfeuille-Michaud. 2008. Crohn's disease-associated *Escherichia coli* LF82 aggravates colitis in injured mouse colon via signaling by flagellin. Inflammatory bowel diseases 14:1051-60.
8. Colome, J. A., J. Jorda, D. Espinos, L. Bruseghini, and A. Esteras. 1998. Effect of N-acetylcysteine on the oxidative burst induced by phagocytosis of bacteria in human leukocytes. Methods and findings in experimental and clinical pharmacology 20:301-5.
9. Darfeuille-Michaud, A., J. Boudeau, P. Bulois, C. Neut, A. L. Glasser, N. Barnich, M. A. Bringer, A. Swidsinski, L. Beaugerie, and J. F. Colombel. 2004. High prevalence of adherent-invasive *Escherichia coli* associated with ileal mucosa in Crohn's disease. Gastroenterology 127:412-21.
10. Darfeuille-Michaud, A., C. Neut, N. Barnich, E. Lederman, P. Di Martino, P. Desreumaux, L. Gambiez, B. Joly, A. Cortot, and J. F. Colombel. 1998. Presence of adherent *Escherichia coli* strains in ileal mucosa of patients with Crohn's disease. Gastroenterology 115:1405-13.
11. De Groote, M. A., D. Granger, Y. Xu, G. Campbell, R. Prince, and F. C. Fang. 1995. Genetic and redox determinants of nitric oxide cytotoxicity in a *Salmonella typhimurium* model. Proceedings of the National Academy of Sciences of the United States of America 92:6399-403.
12. de la Huerga, J., and H. Popper. 1951. Urinary excretion of choline metabolites following choline administration in normals and patients with hepatobiliary diseases. The Journal of clinical investigation 30:463-70.
13. Dudhgaonkar, S. P., S. K. Tandan, D. Kumar, M. Raviprakash, and M. Kataria. 2007. Influence of simultaneous inhibition of cyclooxygenase-2 and inducible nitric oxide synthase in experimental colitis in rats. Inflammopharmacology 15:188-95.
14. Eckburg, P. B., E. M. Bik, C. N. Bernstein, E. Purdom, L. Dethlefsen, M. Sargent, S. R. Gill, K. E. Nelson, and D. A. Reiman. 2005. Diversity of the human intestinal microbial flora. Science 308:1635-8.
15. Enocksson, A., J. Lundberg, E. Weitzberg, A. Norrby-Teglund, and B. Svenungsson. 2004. Rectal nitric oxide gas and stool cytokine levels during the course of infectious gastroenteritis. Clinical and diagnostic laboratory immunology 11:250-4.
16. Faith, J. J., N. P. McNulty, F. E. Rey, and J. I. Gordon. 2011. Predicting a human gut microbiota's response to diet in gnotobiotic mice. Science 333:101-4.
17. Fischbach, M. A., and J. L. Sonnenburg. 2011. Eating for two: how metabolism establishes interspecies interactions in the gut. Cell host & microbe 10:336-47.
18. Flo, T. H., K. D. Smith, S. Sato, D. J. Rodriguez, M. A. Holmes, R. K. Strong, S. Akira, and A. Aderem. 2004. Lipocalin 2 mediates an innate immune response to bacterial infection by sequestrating iron. Nature 432:917-21.
19. Frank, D. N., A. L. St Amand, R. A. Feldman, E. C. Boedeker, N. Harpaz, and N. R. Pace. 2007. Molecular-phylogenetic characterization of microbial community imbalances in human inflammatory bowel diseases. Proc Natl Acad Sci USA 104:13780-5.
20. Garrett, W. S., C. A. Gallini, T. Yatsunenko, M. Michaud, A. DuBois, M. L. Delaney, S. Punit, M. Karlsson, L. Bry, J. N. Glickman, J. I. Gordon, A. B. Onderdonk, and L. H. Glimcher. 2010. Enterobacteriaceae act in concert with the gut microbiota to induce spontaneous and maternally transmitted colitis. Cell Host Microbe 8:292-300.
21. Garrett, W. S., G. M. Lord, S. Punit, G. Lugo-Villarino, S. K. Mazmanian, S. Ito, J. N. Glickman, and L. H. Glimcher. 2007. Communicable ulcerative colitis induced by T-bet deficiency in the innate immune system. Cell 131:33-45.
22. Gennis, R. B., and V. Stewart. 1996. Respiration, p. 217-261. In F. C. Neidhardt, R. Curtiss III, J. L. Ingraham, E. C. C. Lin, K. B. Low, B. Magasanik, W. S. Reznikoff, M. Riley, M. Schaechter, and H. E. Umbarger (ed.), *Escherichia coli* and *Salmonella*. Cellular and molecular biology, 2nd ed, vol. 1. ASM Press, Washington, D.C.
23. Giaffer, M. H., C. D. Holdsworth, and B. I. Duerden. 1991. The assessment of faecal flora in patients with inflammatory bowel disease by a simplified bacteriological technique. Journal of medical microbiology 35:238-43.
24. Goetz, D. H., M. A. Holmes, N. Borregaard, M. E. Bluhm, K. N. Raymond, and R. K. Strong. 2002. The neutrophil lipocalin NGAL is a bacteriostatic agent that interferes with siderophore-mediated iron acquisition. Mol Cell 10:1033-43.
25. Gophna, U., K. Sommerfeld, S. Gophna, W. F. Doolittle, and S. J. Veldhuyzen van Zanten. 2006. Differences between tissue-associated intestinal microfloras of patients with Crohn's disease and ulcerative colitis. J Clin Microbiol 44:4136-41.
26. Guandalini, G. S., L. Zhang, E. Fornero, J. A. Centeno, V. P. Mokashi, P. A. Ortiz, M. D. Stockelman, A. R. Osterburg, and G. G. Chapman. 2011. Tissue distribution of tungsten in mice following oral exposure to sodium tungstate. Chemical research in toxicology 24:488-93.
27. Hanzu, F., R. Gomis, M. J. Coves, J. Viaplana, M. Palomo, A. Andreu, J. Szpunar, and J. Vidal. 2010. Proof-of-concept trial on the efficacy of sodium tungstate in human obesity. Diabetes, obesity & metabolism 12:1013-8.
28. Harper, R. W., C. Xu, J. P. Eiserich, Y. Chen, C. Y. Kao, P. Thai, H. Setiadi, and R. Wu. 2005. Differential regulation of dual NADPH oxidases/peroxidases, Duox1 and Duox2, by Th1 and Th2 cytokines in respiratory tract epithelium. FEBS letters 579:4911-7.
29. Hartman, A. L., D. M. Lough, D. K. Barupal, O. Fiehn, T. Fishbein, M. Zasloff, and J. A. Eisen. 2009. Human gut microbiome adopts an alternative state following small bowel transplantation. Proc Natl Acad Sci USA 106:17187-92.
30. Hohn, D. C., and R. I. Lehrer. 1975. NADPH oxidase deficiency in X-linked chronic granulomatous disease. The Journal of clinical investigation 55:707-13.
31. Jagannath, C., J. K. Actor, and R. L. Hunter, Jr. 1998. Induction of nitric oxide in human monocytes and monocyte cell lines by *Mycobacterium tuberculosis*. Nitric oxide:biology and chemistry/official journal of the Nitric Oxide Society 2:174-86.
32. Jones, S. A., T. Gibson, R. C. Maltby, F. Z. Chowdhury, V. Stewart, P. S. Cohen, and T. Conway. 2011. Anaerobic respiration of *Escherichia coli* in the mouse intestine. Infection and immunity 79:4218-26.
33. Koch, T., S. Heller, S. Heissler, I. Breil, H. G. Schiefer, K. van Ackern, and H. Neuhof. 1996. Effects of N-ace- 34. Koropatkin, N. M., E. A. Cameron, and E. C. Martens. 2012. How glycan metabolism shapes the human gut microbiota. Nature reviews. Microbiology 10:323-35.
35. Krook, A., B. Lindstrom, J. Kjellander, G. Jarnerot, and L. Bodin. 1981. Relation between concentrations of metronidazole and Bacteroides spp in faeces of patients with Crohn's disease and healthy individuals. Journal of clinical pathology 34:645-50.
36. Kuwano, Y., T. Kawahara, H. Yamamoto, S. Teshima-Kondo, K. Tominaga, K. Masuda, K. Kishi, K. Morita, and K. Rokutan. 2006. Interferon-gamma activates transcription of NADPH oxidase 1 gene and upregulates production of superoxide anion by human large intestinal epithelial cells. American journal of physiology. Cell physiology 290:C433-43.
37. Ley, R. E., F. Backhed, P. Turnbaugh, C. A. Lozupone, R. D. Knight, and J. I. Gordon. 2005. Obesity alters gut microbial ecology. Proceedings of the National Academy of Sciences of the United States of America 102:11070-5.
38. Lundberg, J. O., P. M. Hellstrom, J. M. Lundberg, and K. Alving. 1994. Greatly increased luminal nitric oxide in ulcerative colitis. Lancet 344:1673-4.
39. Lupp, C., M. L. Robertson, M. E. Wickham, I. Sekirov, O. L. Champion, E. C. Gaynor, and B. B. Finlay. 2007. Host-mediated inflammation disrupts the intestinal microbiota and promotes the overgrowth of Enterobacteriaceae. Cell Host Microbe 2:119-29.
40. Mahowald, M. A., F. E. Rey, H. Seedorf, P. J. Turnbaugh, R. S. Fulton, A. Wollam, N. Shah, C. Wang, V. Magrini, R. K. Wilson, B. L. Cantarel, P. M. Coutinho, B. Henrissat, L. W. Crock, A. Russell, N. C. Verberkmoes, R. L. Hettich, and J. I. Gordon. 2009. Characterizing a model human gut microbiota composed of members of its two dominant bacterial phyla. Proceedings of the National Academy of Sciences of the United States of America 106:5859-64.
41. Martinez, I., J. Kim, P. R. Duffy, V. L. Schlegel, and J. Walter. 2010. Resistant starches types 2 and 4 have differential effects on the composition of the fecal microbiota in human subjects. PloS one 5:e15046.
42. Masoodi, I., R. Kochhar, U. Dutta, C. Vaishnavi, K. K. Prasad, K. Vaiphei, S. Kaur, and K. Singh. 2009. Fecal lactoferrin, myeloperoxidase and serum C-reactive are effective biomarkers in the assessment of disease activity and severity in patients with idiopathic ulcerative colitis. J Gastroenterol Hepatol 24:1768-74.
43. McPhail, L. C., L. R. DeChatelet, P. S. Shirley, C. Wilfert, R. B. Johnston, Jr., and C. E. McCall. 1977. Deficiency of NADPH oxidase activity in chronic granulomatous disease. The Journal of pediatrics 90:213-7.
44. Nagy, A. M., F. Vanderbist, N. Parij, P. Maes, P. Fondu, and J. Neve. 1997. Effect of the mucoactive drug nacystelyn on the respiratory burst of human blood polymorphonuclear neutrophils. Pulmonary pharmacology & therapeutics 10:287-92.
45. Palmer, R. M., D. S. Ashton, and S. Moncada. 1988. Vascular endothelial cells synthesize nitric oxide from L-arginine. Nature 333:664-6.
46. Peterson, D. A., D. N. Frank, N. R. Pace, and J. I. Gordon. 2008. Metagenomic approaches for defining the pathogenesis of inflammatory bowel diseases. Cell host & microbe 3:417-27.
47. Raffatellu, M., M. D. George, Y. Akiyama, M. J. Hornsby, S. P. Nuccio, T. A. Paixao, B. P. Butler, H. Chu, R. L. Santos, T. Berger, T. W. Mak, R. M. Tsolis, C. L. Bevins, J. V. Solnick, S. Dandekar, and A. J. Baumler. 2009. Lipocalin-2 resistance confers an advantage to *Salmonella enterica* serotype *Typhimurium* for growth and survival in the inflamed intestine. Cell Host Microbe 5:476-86.
48. Sadlack, B., H. Merz, H. Schorle, A. Schimpl, A. C. Feller, and I. Horak. 1993. Ulcerative colitis-like disease in mice with a disrupted interleukin-2 gene. Cell 75:253-61.
49. Sadowska, A. M., B. Manuel-y-Keenoy, T. Vertongen, G. Schippers, D. Radomska-Lesniewska, E. Heytens, and W. A. De Backer. 2006. Effect of N-acetylcysteine on neutrophil activation markers in healthy volunteers: in vivo and in vitro study. Pharmacological research: the official journal of the Italian Pharmacological Society 53:216-25.
50. Salzman, A., A. G. Denenberg, I. Ueta, M. O'Connor, S. C. Linn, and C. Szabo. 1996. Induction and activity of nitric oxide synthase in cultured human intestinal epithelial monolayers. The American journal of physiology 270:G565-73.
51. Schoneich, C. 2005. Methionine oxidation by reactive oxygen species: reaction mechanisms and relevance to Alzheimer's disease. Biochimica et biophysica acta 1703:111-9.
52. Seger, R. A., L. Tiefenauer, T. Matsunaga, A. Wildfeuer, and P. E. Newburger. 1983. Chronic granulomatous disease due to granulocytes with abnormal NADPH oxidase activity and deficient cytochrome-b. Blood 61:423-8.
53. Seksik, P., L. Rigottier-Gois, G. Gramet, M. Sutren, P. Pochart, P. Marteau, R. Jian, and J. Dore. 2003. Alterations of the dominant faecal bacterial groups in patients with Crohn's disease of the colon. Gut 52:237-42.
54. Sellon, R. K., S. Tonkonogy, M. Schultz, L. A. Dieleman, W. Grenther, E. Balish, D. M. Rennick, and R. B. Sartor. 1998. Resident enteric bacteria are necessary for development of spontaneous colitis and immune system activation in interleukin-10-deficient mice. Infect Immun 66:5224-31.
55. Singer, II, D. W. Kawka, S. Scott, J. R. Weidner, R. A. Mumford, T. E. Riehl, and W. F. Stenson. 1996. Expression of inducible nitric oxide synthase and nitrotyrosine in colonic epithelium in inflammatory bowel disease. Gastroenterology 111:871-85.
56. Sonnenburg, E. D., H. Zheng, P. Joglekar, S. K. Higginbottom, S. J. Firbank, D. N. Bolam, and J. L. Sonnenburg. 2010. Specificity of polysaccharide use in intestinal bacteroides species determines diet-induced microbiota alterations. Cell 141:1241-52.
57. Stecher, B., S. Chaffron, R. Kappeli, S. Hapfelmeier, S. Freedrich, T. C. Weber, J. Kirundi, M. Suar, K. D. McCoy, C. von Mering, A. J. Macpherson, and W. D. Hardt. 2010. Like will to like: abundances of closely related species can predict susceptibility to intestinal colonization by pathogenic and commensal bacteria. PLoS pathogens 6:e1000711.
58. Stecher, B., R. Robbiani, A. W. Walker, A. M. Westendorf, M. Barthel, M. Kremer, S. Chaffron, A. J. Macpherson, J. Buer, J. Parkhill, G. Dougan, C. von Mering, and W. D. Hardt. 2007. *Salmonella enterica* serovar *typhimurium* exploits inflammation to compete with the intestinal microbiota. PLoS Biol 5:2177-89.
59. Stewart, V., Y. Lu, and A. J. Darwin. 2002. Periplasmic nitrate reductase (NapABC enzyme) supports anaerobic respiration by *Escherichia coli* K-12. J Bacteriol 184:1314-23.

60. Szabo, C., H. Ischiropoulos, and R. Radi. 2007. Peroxynitrite: biochemistry, pathophysiology and development of therapeutics. Nat Rev Drug Discov 6:662-80.
61. Takahashi, H., and A. Nason. 1957. Tungstate as competitive inhibitor of molybdate in nitrate assimilation and in N2 fixation by Azotobacter. Biochimica et biophysica acta 23:433-5.
62. Thiennimitr, P., S. E. Winter, M. G. Winter, M. N. Xavier, V. Tolstikov, D. L. Huseby, T. Sterzenbach, R. M. Tsolis, J. R. Roth, and A. J. Baumler. 2011. Intestinal inflammation allows Salmonella to use ethanolamine to compete with the microbiota. Proceedings of the National Academy of Sciences of the United States of America 108:17480-5.
63. Walker, A. W., J. Ince, S. H. Duncan, L. M. Webster, G. Holtrop, X. Ze, D. Brown, M. D. Stares, P. Scott, A. Bergerat, P. Louis, F. McIntosh, A. M. Johnstone, G. E. Lobley, J. Parkhill, and H. J. Flint. 2011. Dominant and diet-responsive groups of bacteria within the human colonic microbiota. The ISME journal 5:220-30.
64. Winter, S. E., P. Thiennimitr, M. G. Winter, B. P. Butler, D. L. Huseby, R. W. Crawford, J. M. Russell, C. L. Bevins, L. G. Adams, R. M. Tsolis, J. R. Roth, and A. J. Baumler. 2010. Gut inflammation provides a respiratory electron acceptor for Salmonella. Nature 467:426-9.
65. Winter, S. E., M. G. Winter, M. N. Xavier, P. Thiennimitr, V. Poon, A. M. Keestra, R. Laughlin, G. Gomez, J. Wu, S. D. Lawhon, I. Popova, S. J. Parikh, L. G. Adams, R. M. Tsolis, V. J. Stewart, and A. J. Bäumler. 2013. Host-derived nitrate boosts growth of E. coli in the inflamed gut. Science:in press.
66. Wu, G. D., J. Chen, C. Hoffmann, K. Bittinger, Y. Y. Chen, S. A. Keilbaugh, M. Bewtra, D. Knights, W. A. Walters, R. Knight, R. Sinha, E. Gilroy, K. Gupta, R. Baldassano, L. Nessel, H. Li, F. D. Bushman, and J. D. Lewis. 2011. Linking long-term dietary patterns with gut microbial enterotypes. Science 334:105-8.
67. Zhu, L., C. Gunn, and J. S. Beckman. 1992. Bactericidal activity of peroxynitrite. Archives of biochemistry and biophysics 298:452-7.

Example 2

Tungstate Treatment of the Dysbiosis Associated with IBD

The human large intestine is host to a complex microbial community dominated by obligate anaerobic bacteria belonging to the phyla Bacteroidetes and Firmicutes. On the phylum level, this microbiota composition is highly conserved, not just during the life span of an individual but also between different mammalian species. However, conditions of intestinal inflammation can lead to a microbial imbalance (dysbiosis) characterized by a marked decrease in the representation of obligate anaerobic bacteria and an increased relative abundance of facultative anaerobic bacteria, such as Enterobacteriaceae (1). Inflammation-associated dysbiosis is thought to exacerbate disease symptoms and duration (2).

Recent work has demonstrated that with the onset of inflammatory host responses, the nutritional environment in the anaerobic gut lumen substantially changes (3,4). Host-generated reactive oxygen and nitrogen species aimed at incapacitating microbes inside the host tissue leak into the intestinal lumen. These radicals quickly react with organic sulfides and tertiary amines present in the intestinal lumen to form the respective S-oxides and N-oxides (5). In addition, peroxynitrite is quickly converted to harmless nitrate (6). Escherichia coli (E. coli), a prototypical member of the Enterobacteriaceae family, can utilize nitrate as well as S-oxides and N-oxides as alternative electron acceptors to perform anaerobic respiration (7). Anaerobic respiration is more efficient than fermentation in generating energy for growth, thus allowing E. coli to outgrow competing obligate anaerobic bacteria that only perform fermentation. Thus, inflammation selectively enhances the growth of commensal Enterobacteriaceae by producing alternative electron acceptors for anaerobic respiration (3).

Figure 9:
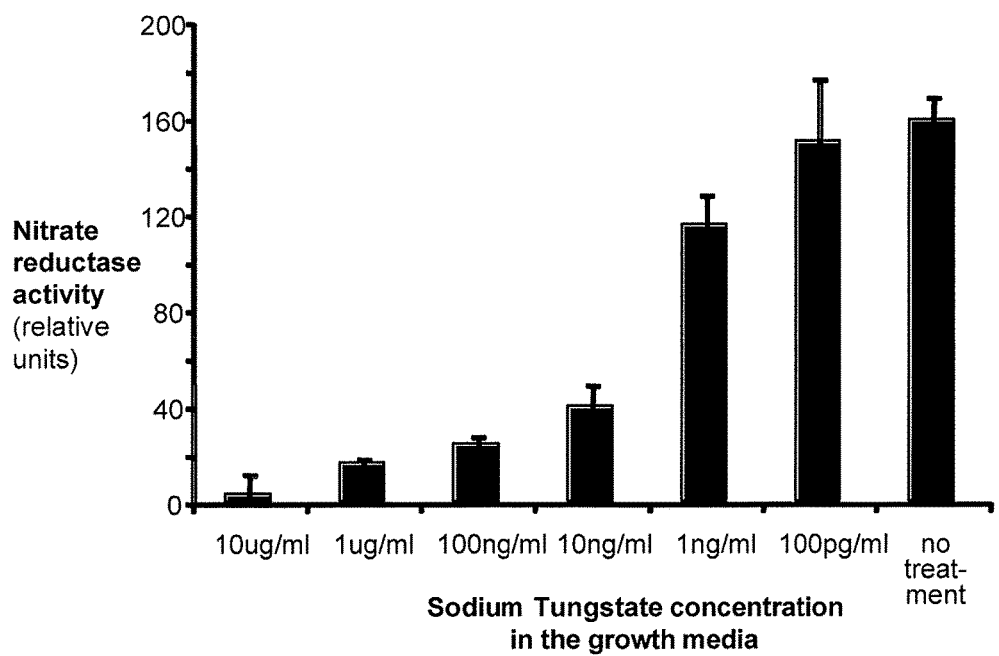
FIG. 9 shows the effect of tungstate on nitrate reductase activity in E. coli Nissle 1917 in vitro.

In E. coli, the respiratory reductases for nitrate, DMSO and TMAO as well as the formate dehydrogenases FdnG and FdoG contain molybdenum (Mo) as a key catalyst for electron transfer reactions (7). The functions of FdnG and FdoG are linked to respiration, because these two formate dehydrogenases couple respiratory electron acceptors to the electron donor formate, a fermentation end product present in the large intestine. Formate dehydrogenases and respiratory reductases contain Mo within a molybdopterin cofactor. Tungsten (W) has chemical properties similar, but not identical, to Mo. In some instances, W can replace Mo in the molybdopterin cofactor, rendering the cofactor and the respiratory enzymes inactive, a method that has been used for various microorganisms to abolish anaerobic respiration under laboratory conditions (8). To test whether the addition of W (as the soluble sodium salt $Na_2WO_4$; sodium tungstate) to bacterial growth media can inhibit anaerobic nitrate respiration, aliquots of LB broth supplemented with 40 mM nitrate and varying concentrations of tungstate were inoculated with the E. coli Nissle 1917 wild-type strain and incubated under microaerobic conditions for 3 h at 37° C. (3). Nitrate reductase activity was assayed using a modified Griess assay (9) (FIG. 9). While robust nitrate reductase activity was measured in mock-treated cultures, significantly reduced reductase activity was present in cultures supplemented with tungstate at concentrations exceeding 10 ng/ml (FIG. 9). These findings show that low concentration of soluble tungstate salt inhibits anaerobic respiratory enzymes in Enterobacteriaceae.

Figure 10:
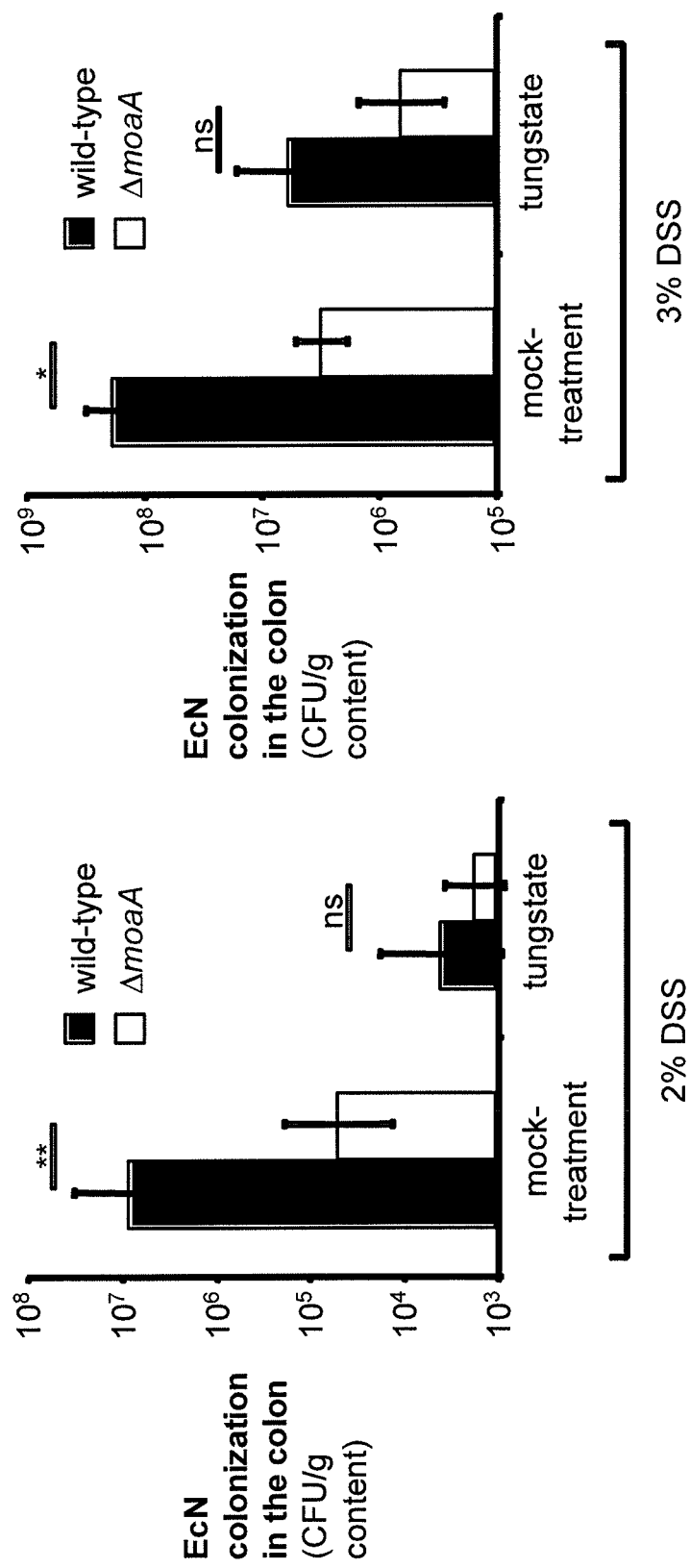
FIG. 10 shows the effect of oral tungstate administration (0.2%) on anaerobic respiration of E. coli Nissle 1917 in the DSS-colitis model. Bacterial load in the colon content was determined 5 days after infection with a 1:1 mixture of the wild-type strain and the anaerobic respiration deficient moaA mutant.

To determine whether the administration of soluble tungsten (W) salts can abolish anaerobic respiration and thus blunt the bloom of Enterobacteriaceae in vivo, a murine model of chemically-induced colitis, the dextran sulfate sodium (DSS) colitis model, was employed. Oral administration of DSS in the drinking water induces a vigorous intestinal inflammatory response that is accompanied by a bloom of commensal Enterobacteriaceae (3). Groups of C57BL/6 mice received DSS-supplemented (2 or 3%) drinking water or received DSS-supplemented (2 or 3%) drinking water with sodium tungstate (0.2%) added. After onset of inflammation (4 days after start of the treatment), mice were intragastrically inoculated with a 1:1 mixture of the E. coli Nissle 1917 wild-type and an isogenic moaA mutant deficient for molybdopterin cofactor biosynthesis. Utilization of these non-pathogenic indicator strains allows a determination of the growth advantage conferred through anaerobic respiration by comparing colonization with the wild-type strain with an anaerobic respiration-deficient mutant (moaA mutant) (3). 5 days after inoculation of mice, animals were euthanized and colonization with the E. coli indicator strains determined by cultivation on selective media (each of the strains is marked with a different antibiotic resistance gene) (FIG. 10). Consistent with the idea that inflammation-derived electron acceptors enhance growth of Enterobacteriaceae, the Nissle 1917 wild-type strain was recovered from the colon content of DSS treated mice in significantly higher numbers than the anaerobic respiration deficient moaA mutant, regardless of the DSS concentration used to induce colitis (FIG. 10). In contrast, administration of sodium tungstate in DSS treated mice significantly diminished the total number of *E. coli* indicator strains and both strains were recovered at similar numbers, indicating that tungstate poisoning of the molybdopterin cofactor diminishes the growth advantage conferred by anaerobic respiration. Moreover, after tungstate treatment the colonization of both the *E. coli* wild-type and the respiration-deficient moaA mutant was similar to that of the moaA mutant in the mock-treated group (DSS only), indicating that tungstate administration specifically blunts the fitness advantage conferred by anaerobic respiration. Taken together, these results show that oral administration of soluble tungsten salts can aid in restoring a normal microbiota composition by specifically inhibiting anaerobic respiratory pathways operational only during gut inflammation.

Figure 11:
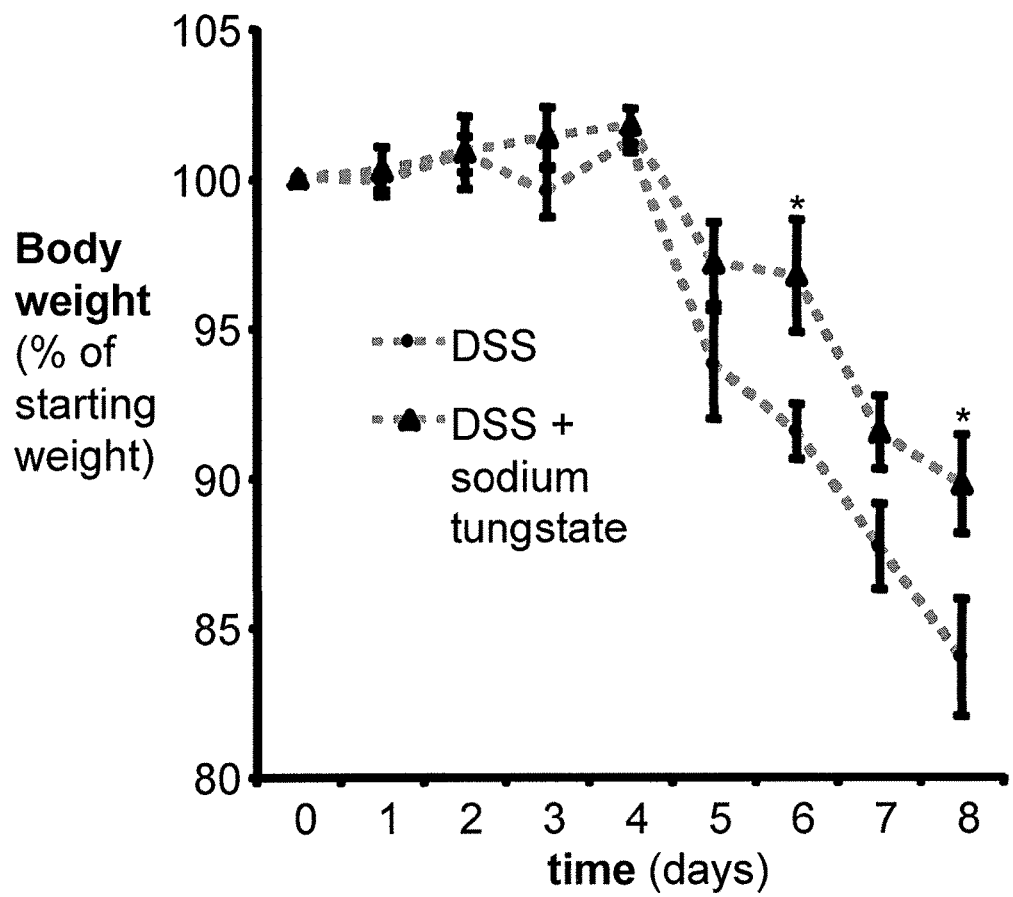
FIG. 11 shows the effect of oral tungstate administration (0.2%) on animal body weight in the DSS-colitis model (3% DSS) over time.

The dysbiosis occurring in intestinal inflammatory disorders can exacerbate the host response and prolong disease episodes (2). To explore whether inhibition of anaerobic respiration through tungsten has any impact on the overall health of the individual, the body weight of the animals treated with 3% DSS was determined (experiment described above) (FIG. 11). DSS-colitis was associated with significant body weight loss (<85% of starting weight after 8 days of DSS treatment), with the beginning of the weight loss coinciding with the onset of intestinal inflammation. Consistent with the idea that tungstate administration can aid in restoring a less insulting, normal community structure, DSS-treated animals that received tungstate in the drinking water displayed significantly less weight loss (>90% of starting weight after 8 days of DSS treatment than the control group (DSS only) (FIG. 11). Collectively, these data demonstrate that oral administration of soluble tungsten salts (at various concentrations) can alleviate disease symptoms during inflammatory disorders of the intestinal tract by specifically preventing anaerobic respiration-driven dysbiosis.

To further test the efficacy of tungstate treatment, *E. coli* indicator strains that were either proficient for anaerobic respiration (*E. coli* Nissle 1917 wild-type) or deficient for nitrate respiration, DMSO respiration, and TMAO respiration due to a mutation in one of the molybdopterin cofactor biosynthesis genes (*E. coli* Nissle 1917 moaA mutant) were used. Groups of mice with DSS-induced colitis were inoculated with an equal mixture of both E. coli indicator strains (i.e., wild-type and moaA mutant) and received either regular water (vehicle control) or drinking water containing 2 g/l sodium tungstate ($Na_2WO_4 \times 2H_2O$; Sigma-Aldrich, St. Louis, Mo., USA) to receive a calculated average dose of 130 mg/kg/day (assuming 2.6 ml of water intake per day for each animal). These experiments determined whether anaerobic respiration would provide a fitness advantage upon the *E. coli* wild-type over the moaA mutant in the inflamed intestine of DSS-treated mice. Furthermore, if tungstate treatment would inhibit anaerobic respiration, these experiments determined whether this fitness advantage would be eliminated and both strains would be recovered at a 1:1 ratio. In other words, the use of *E. coli* indicator strains as described herein enabled the determination of whether tungstate treatment would block growth by anaerobic respiration in vivo.

Figure 12A:
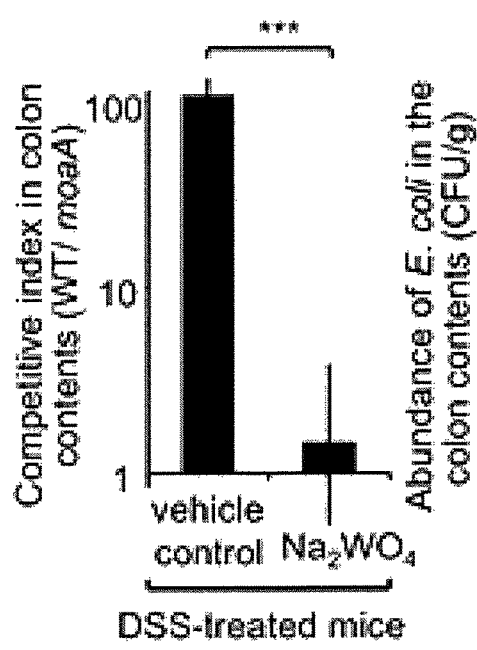
FIGS. 12A-B show that tungstate treatment blocks a bloom of commensal E. coli indicator strains by preventing anaerobic respiration in DSS-treated mice. (12A) Competitive index (ratio of wild-type to moaA mutant) recovered from colon contents of DSS-treated mice inoculated with an equal mixture of both indicator strains. Mice received water (vehicle control) or water containing sodium tungstate ($Na_2WO_4$). (12B) Absolute numbers of E. coli recovered from colon contents of conventional mice (mock treatment), or mice receiving DSS alone (DSS) or in combination with sodium tungstate (DSS+$Na_2WO_4$). ***, $P<0.001$.

In mice with DSS-induced colitis (vehicle control), the *E. coli* wild-type strain was recovered in approximately 100-fold higher numbers than the anaerobic respiration-deficient moaA mutant. In contrast, both strains were recovered in equal numbers from mice with DSS-induced colitis that had received sodium tungstate ($Na_2WO_4$) (FIG. 12A). Thus, the use of *E. coli* indicator strains demonstrated that tungstate treatment completely abrogated the fitness advantage conferred by anaerobic respiration in the lumen of the inflamed gut.

Figure 13A:
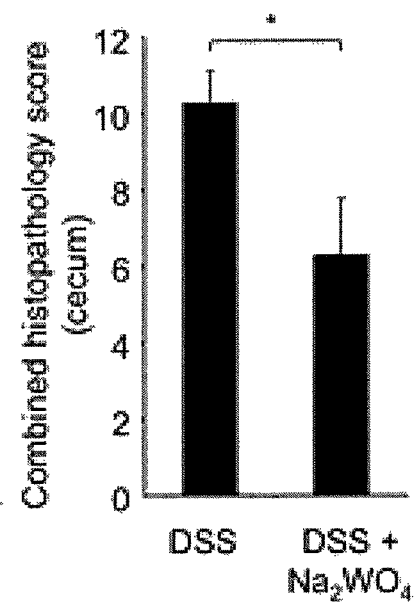
FIGS. 13A-D show that tungstate treatment reduces intestinal inflammation in DSS-treated mice. (13A-C) Conventional mice received 4% DSS alone (DSS) or in combination with sodium tungstate (DSS+$Na_2WO_4$) for 9 days. (13D) Germ-free mice received 1% DSS or 1% DSS+$Na_2WO_4$ for five days. (13A) Average histopathology score from the cecum. (13B-D) Transcript levels of Tnfa (B) and Kc (13C and 13D) in the cecal mucosa were determined by real-time PCR. *, $P<0.05$; ***, $P<0.001$; ns, not statistically significantly different.

Importantly, tungstate treatment resulted in a significant ($P<0.05$) reduction in the overall pathology score of the cecal mucosa, which was determined by a veterinary pathologist using blinded scoring of sections from DSS-treated mice (FIG. 13A). Furthermore, tungstate treatment resulted in a blunting of transcript levels of Tnfa, encoding tumor necrosis factor $\alpha$ (FIG. 13B), and abrogated induction of Kc, the gene encoding the neutrophil chemoattractant CXCL1 (FIG. 13C), in the cecal mucosa. This reduction was remarkable, because DSS treatment induces cecal inflammation by a mechanism that is only partially dependent on the presence of microbiota (10). In other words, DSS treatment causes inflammation in germ-free mice, but inflammation is exacerbated by the presence of microbiota. Thus, by inhibiting the microbiota-dependent component of inflammation, one can only expect to achieve a reduction in inflammation, but not a resolution of inflammation. Thus, given the marked pathology observed in DSS-treated germ-free mice (10), the reduction of cecal pathology after tungsten treatment was remarkable. Collectively, these data show that blocking anaerobic respiration prevents a bloom of Enterobacteriaceae, thereby reducing intestinal inflammation.

Figure 12B:
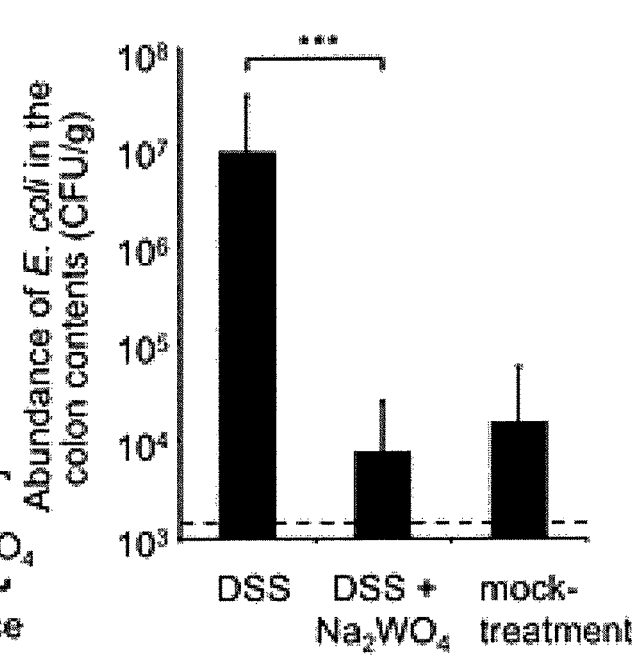
Figure 13B:
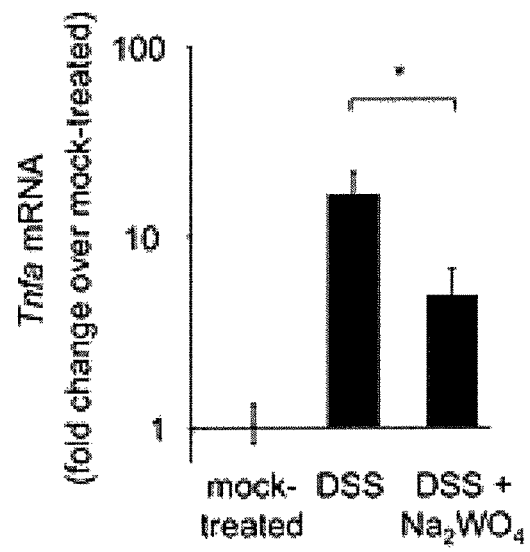
Figure 13C:
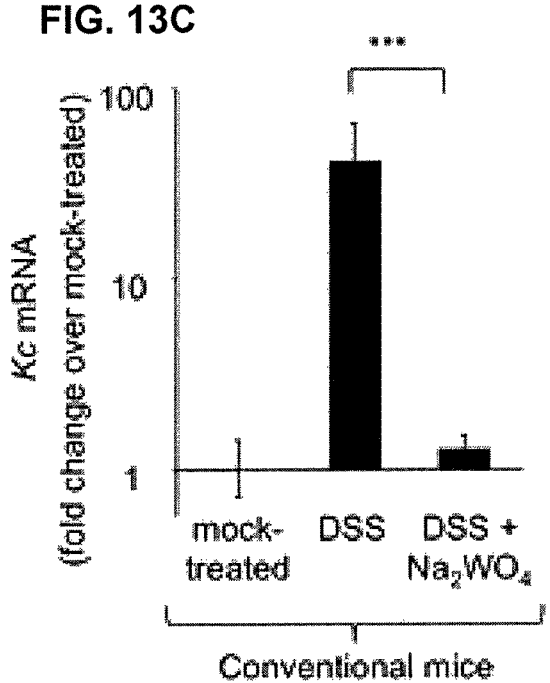

These experiments with *E. coli* indicator strains demonstrated that tungstate treatment prevented facultative anaerobic bacteria from blooming during inflammation by preventing anaerobic respiration (FIGS. 12A and 12B). Preventing this bloom correlated with a reduced severity of inflammatory lesions in the cecal mucosa (FIG. 13A) and reduced transcript levels of pro-inflammatory genes (FIGS. 13B and 13C). There are two possible explanations for this observation. First, a bloom of facultative anaerobic bacteria exacerbates inflammation, and tungstate treatment reduced inflammation by preventing this bloom. Second, it is formally possible that sodium tungstate has anti-inflammatory properties of its own, independently of microbes.

Figure 13D:
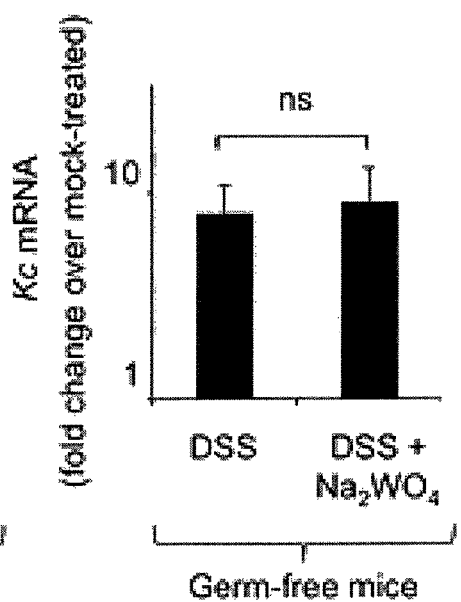

The key experiment to distinguish between these two possibilities is to test whether tungstate treatment reduces inflammation in germ-free mice. To this end, groups of four germ-free mice were treated with 1% DSS, 1% DSS+sodium tungstate, or drinking water without supplementation. Unlike in conventional mice (FIG. 13C), tungstate treatment did not reduce levels of pro-inflammatory cytokines in germ-free mice 5 days after the beginning of DSS treatment (FIG. 13D). These data illustrate that tungstate treatment blunts cytokine levels in DSS-treated mice through a microbiota-dependent mechanism. Thus, these data demonstrate that the mechanism by which tungstate reduces intestinal inflammation depends on the presence of gut-associated microbial communities.

The development of intestinal inflammation (induced by DSS treatment or oxazolone-treatment) can be associated with changes in bacterial communities over time. Furthermore, communities associated with severe DSS-induced or oxazolone-induced colitis can cluster away from communities recovered from mock-treated groups or from animals prior to treatment. One of the prominent changes associated with inflammation is an increased abundance of facultative anaerobic bacteria (Lupp et al., *Cell Host Microbe*, 2:119-29 (2007)). Importantly, this change is not observed in communities recovered from mice with severe colitis that were treated with tungstate. The prevalence of facultative anaerobic bacteria in communities recovered from Nos2-deficient mice with colitis is also reduced compared to communities recovered from wild-type mice with colitis. Thus, the data described in this example illustrate that anaerobic respiration is an important driver of phylum-level changes in the composition of microbial communities during gut inflammation. Furthermore, these results show that an inhibition of anaerobic respiration is a viable strategy for restoring a normal microbial community structure. Moreover, these results show that the mechanism by which tungstate reduces intestinal inflammation depends on the presence of gut-associated microbial communities.

References

1 P. B. Eckburg, E. M. Bik, C. N. Bernstein et al., Diversity of the human intestinal microbial flora, *Science* 308 (5728), 1635 (2005); D. A. Peterson, D. N. Frank, N. R. Pace et al., Metagenomic approaches for defining the pathogenesis of inflammatory bowel diseases, *Cell Host Microbe* 3 (6), 417 (2008).

2 W. S. Garrett, G. M. Lord, S. Punit et al., Communicable ulcerative colitis induced by T-bet deficiency in the innate immune system, *Cell* 131 (1), 33 (2007); W. S. Garrett, C. A. Gallini, T. Yatsunenko et al., Enterobacteriaceae act in concert with the gut microbiota to induce spontaneous and maternally transmitted colitis, *Cell Host Microbe* 8 (3), 292 (2010).

3 S. E. Winter, M. G. Winter, M. N. Xavier et al., Host-derived nitrate boosts growth of *E. coli* in the inflamed gut, *Science* 339 (6120), 708 (2013).

4 S. E. Winter, P. Thiennimitr, M. G. Winter et al., Gut inflammation provides a respiratory electron acceptor for *Salmonella*, *Nature* 467 (7314), 426 (2010).

5 C. Schoneich, Methionine oxidation by reactive oxygen species: reaction mechanisms and relevance to Alzheimer's disease, *Biochim Biophys Acta* 1703 (2), 111 (2005); B. Clement and T. Kunze, Microsomal N-oxygenation of adenine to adenine 1-N-oxide, *Arch Pharm (Weinheim)* 326 (1), 25 (1993).

6 C. Szabo, H. Ischiropoulos, and R. Radi, Peroxynitrite: biochemistry, pathophysiology and development of therapeutics, *Nat Rev Drug Discov* 6 (8), 662 (2007).

7 R. B. Gennis and Stewart V., Respiration, p. 217-261, In F. C. Neidhardt, R. Curtiss III, J. L. Ingraham, E. C. C. Lin, K. B. Low, B. Magasanik, W. S. Reznikoff, M. Riley, M. Schaechter, and H. E. Umbarger (ed), *Escherichia coli* and *Salmonella. Cellular and molecular biology*, 2nd ed, vol. 1. ASM Press, Washington, D.C. (1996).

8 F. Gutthann, M. Egert, A. Marques et al., Inhibition of respiration and nitrate assimilation enhances photohydrogen evolution under low oxygen concentrations in *Synechocystis* sp. PCC 6803, *Biochim Biophys Acta* 1767 (2), 161 (2007); C. Baraquet, L. Theraulaz, C. lobbi-Nivol et al., Unexpected chemoreceptors mediate energy taxis towards electron acceptors in *Shewanella oneidensis*, *Mol Microbiol* 73 (2), 278 (2009).

9 V. Stewart and J. Parales, Jr., Identification and expression of genes narL and narX of the nar (nitrate reductase) locus in *Escherichia coli* K-12, *J Bacteriol* 170 (4), 1589 (1988).

10. Kitajima, S., Morimoto, M., Sagara, E., Shimizu, C., and Ikeda, Y., Dextran sodium sulfate-induced colitis in germ-free IQI/Jic mice. *Exp Anim* 50, 387-395 (2001).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for reducing gastrointestinal inflammation in a subject in need thereof, the method comprising orally administering to the subject a therapeutically effective amount of a tungstate salt, wherein the gastrointestinal inflammation is caused by an increased abundance of Enterobacteriaceae present in the subject's gastrointestinal tract, and wherein the therapeutically effective amount of the tungstate salt reduces the gastrointestinal inflammation by reducing the abundance of Enterobacteriaceae in the subject's gastrointestinal tract.

2. The method of claim 1, wherein the gastrointestinal inflammation comprises inflammatory bowel disease (IBD).

3. The method of claim 1, wherein the gastrointestinal inflammation comprises colitis.

4. The method of claim 1, wherein the gastrointestinal inflammation comprises HIV enteropathy.

5. The method of claim 1, wherein the abundance of Enterobacteriaceae in the subject's gastrointestinal tract is reduced by at least about 50% compared to the abundance of Enterobacteriaceae in the subject's gastrointestinal tract prior to receiving the tungstate salt.

6. The method of claim 1, wherein the abundance of Enterobacteriaceae in the subject's gastrointestinal tract is reduced by at least about 80% compared to the abundance of Enterobacteriaceae in the subject's gastrointestinal tract prior to receiving the tungstate salt.

7. The method of claim 1, wherein the tungstate salt is selected from the group consisting of sodium tungstate, potassium tungstate, magnesium tungstate, calcium tungstate, and mixtures thereof.

8. The method of claim 1, wherein the therapeutically effective amount is about 100 mg twice daily for about 6 weeks.

9. The method of claim 1, wherein the tungstate salt is formulated as a pharmaceutical composition.

* * * * *